(12) United States Patent
Kawato et al.

(10) Patent No.: US 10,959,640 B2
(45) Date of Patent: Mar. 30, 2021

(54) APPARATUS AND METHOD FOR SUPPORTING BRAIN FUNCTION ENHANCEMENT

(71) Applicant: ADVANCED TELECOMMUNICATIONS RESEARCH INSTITUTE INTERNATIONAL, Kyoto (JP)

(72) Inventors: Mitsuo Kawato, Soraku-gun (JP); Takeo Watanabe, Soraku-gun (JP); Kazuhisa Shibata, Soraku-gun (JP); Yuka Sasaki, Soraku-gun (JP)

(73) Assignee: ADVANCED TELECOMMUNICATIONS RESEARCH INSTITUTE INTERNATIONAL, Kyoto (JP)

( * ) Notice: Subject to any disclaimer, the term of this patent is extended or adjusted under 35 U.S.C. 154(b) by 0 days.

(21) Appl. No.: 14/232,150

(22) PCT Filed: Oct. 31, 2012

(86) PCT No.: PCT/JP2012/078136
§ 371 (c)(1),
(2) Date: Jan. 10, 2014

(87) PCT Pub. No.: WO2013/069517
PCT Pub. Date: May 16, 2013

(65) Prior Publication Data
US 2014/0171757 A1    Jun. 19, 2014

(30) Foreign Application Priority Data
Nov. 8, 2011   (JP) .............................. JP2011-244048

(51) Int. Cl.
A61B 5/0482      (2006.01)
A61B 5/055       (2006.01)
(Continued)

(52) U.S. Cl.
CPC .......... *A61B 5/0482* (2013.01); *A61B 5/0006* (2013.01); *A61B 5/0075* (2013.01);
(Continued)

(58) Field of Classification Search
CPC .......................... A61B 5/0482; G01R 33/4806
(Continued)

(56) References Cited

U.S. PATENT DOCUMENTS 6,171,239 B1 * 1/2001 Humphrey ..................... 600/372
6,996,261 B2 * 2/2006 deCharms .............. A61B 5/055
378/4

(Continued)

FOREIGN PATENT DOCUMENTS

EP    1 665 988 A1    6/2006
JP    2002-125945 A    5/2002
(Continued)

OTHER PUBLICATIONS

Gilleade, K., Dix, A., & Allanson, J. (2005). Affective videogames and modes of affective gaming: assist me, challenge me, emote me. In Changing Views—Worlds in Play. Presented at DiGRA 2005.*
(Continued)

Primary Examiner — Jerry-Daryl Fletcher
Assistant Examiner — Daniel E Lane
(74) Attorney, Agent, or Firm — Birch, Stewart, Kolasch & Birch, LLP.

(57) ABSTRACT

A training apparatus 1000 using a method of decoding nerve activity includes: a brain activity detecting device 108 for detecting brain activity at a prescribed area within a brain of a subject; and an output device 130 for presenting neurofeedback information (presentation information) to the subject. A processing device 102 decodes a pattern of cranial nerve activity, generates a reward value based on a degree of similarity of the decoded pattern with respect to a target
(Continued)

activation pattern obtained in advance for the event as the object of training, and generates presentation information corresponding to the reward value.

7 Claims, 22 Drawing Sheets

(51) Int. Cl.
| | |
|---|---|
| *A61B 5/04* | (2006.01) |
| *A61B 5/0484* | (2006.01) |
| *A61B 5/0476* | (2006.01) |
| *G01R 33/48* | (2006.01) |
| *A61B 5/00* | (2006.01) |
| *G06F 3/01* | (2006.01) |
| *A61M 21/00* | (2006.01) |
| *A61M 21/02* | (2006.01) |

(52) U.S. Cl.
CPC ...... *A61B 5/04001* (2013.01); *A61B 5/04008* (2013.01); *A61B 5/04012* (2013.01); *A61B 5/0484* (2013.01); *A61B 5/055* (2013.01); *A61B 5/4064* (2013.01); *A61B 5/486* (2013.01); *A61B 5/7246* (2013.01); *A61B 5/742* (2013.01); *G01R 33/4806* (2013.01); *G06F 3/015* (2013.01); *A61B 5/0042* (2013.01); *A61B 5/0476* (2013.01); *A61B 5/7267* (2013.01); *A61B 2505/09* (2013.01); *A61B 2576/026* (2013.01); *A61M 21/02* (2013.01); *A61M 2021/0022* (2013.01); *A61M 2021/0027* (2013.01); *A61M 2021/0044* (2013.01); *A61M 2230/005* (2013.01); *A61M 2230/10* (2013.01)

(58) Field of Classification Search
USPC ........................................ 600/301, 545, 410
See application file for complete search history.

(56) References Cited

U.S. PATENT DOCUMENTS

| | | | | |
|---|---|---|---|---|
| 2002/0042563 | A1* | 4/2002 | Becerra | A61B 5/055 600/407 |
| 2002/0103428 | A1* | 8/2002 | deCharms | 600/410 |
| 2002/0103429 | A1* | 8/2002 | deCharms | 600/410 |
| 2004/0092809 | A1* | 5/2004 | DeCharms | 600/410 |
| 2004/0191747 | A1 | 9/2004 | Atsumori et al. | |
| 2005/0020933 | A1 | 1/2005 | Sato | |
| 2005/0033154 | A1* | 2/2005 | deCharms | G01R 33/4806 600/410 |
| 2005/0283053 | A1* | 12/2005 | deCharms | A61B 5/055 600/300 |
| 2007/0191704 | A1* | 8/2007 | DeCharms | G01R 33/4806 600/411 |
| 2008/0167571 | A1* | 7/2008 | Gevins | 600/544 |
| 2010/0094097 | A1 | 4/2010 | Liu et al. | |
| 2013/0130799 | A1* | 5/2013 | Van Hulle | A61B 5/04842 463/36 |
| 2013/0338526 | A1* | 12/2013 | Howard | 600/544 |

FOREIGN PATENT DOCUMENTS

| | | |
|---|---|---|
| JP | 2004-294593 A | 10/2004 |
| JP | 2005-13442 A | 1/2005 |
| JP | 2005-278685 A | 10/2005 |
| JP | 2007-20835 A | 2/2007 |
| JP | 2007-264055 A | 10/2007 |
| JP | 2008-178546 A | 8/2008 |
| WO | WO 03/057035 A1 | 7/2003 |

OTHER PUBLICATIONS

McGraw-Hill Dictionary of Scientific and Technical Terms 396 (6th ed. 2003) ("McGraw-Hill Dictionary").*
M. Sato, et al. "Hierarchical of Bayesian estimation for MEG inverse problem," NeuroImage, vol. 23, pp. 806-826, 2004.
Miyawaki, Y. et al., "Visual Image Reconstruction from Human Brain Activity Using a Combination of Multiscale Local Image Decoders" Neuron 60, Dec. 11, 2008, pp. 915-929.
Nozomi Ito, et al. "Chikaku Gakushu ni okeru Kinnen no Seika" (Recent Developments in Perceptual Learning), Vision, vol. 22, No. 2, pp. 115-121, 2010 with English translation.
Shibata Kasuhisa et al., Perceptual Learning Incepted by Decoded fMRI Neurofeedback Without Stimulus Presentation, Science, Dec. 9, 2011, vol. 334, pp. 1413-1415.
Stephan Waldert, et al. "A review on directional information in neural signals for brain-machine interfaces", Journal of Physiology—Paris, 103 (2009) pp. 244-254.
T. Watanabe, et al. "Greater plasticity in lower-level than higher-level visual motion processing in a passive perceptual learning task" Nature Neuroscience, 5, (advanced online publication pp. 1-7) 2002.
Yoshioka, et al. "Evaluation of hierarchical Bayesian method through retinotopic brain activities reconstruction from fMRI and MEG signals," NeuroImage, vol. 42, pp. 1397-1413, 2008.
S. Bray et al.: "Direct Instrumental Conditioning of Neural Activity Using Functional Magnetic Resonance Imaging—Derived Reward Feedback", Journal of Neuroscience, vol. 27, No. 28, Jul. 11, 2007, pp. 7498-7507, ISSN: 0270-6474, DOI: 10.1523/JNEUROSCI.2118-07.2007.
Schalk et al.: "Brain-computer interfaces (BCIs): Detection instead of classification", Journal of Neuroscience Methods, Elsevier Science Publisher B.V., Amsterdam, NL, vol. 167, No. 1, Nov. 29, 2007, pp. 51-62, ISSN: 0165-0270, DOI: 10.1016/J.JNEUMETH. 2007.08.010.
DeCharms, et al. "Control over brain activation and pain learned by using real-time functional MRI"; PNAS, Dec. 20, 2005, vol. 102, No. 51, pp. 18626-18631.
Sagara, et al. "Brain Communication—Theory and Application"; Edited by the Institute of Electronics, Information and Communication Engineers, published by Corona-sha, 1st edition, Apr. 25, 2011, pp. 120-122.
Decharms, "Applications of real-time fMRI", Nature Reviews Neuroscience, vol. 9, Sep. 2008, pp. 720-729.
Gerven et al., "The brain-computer interface cycle", J. Neural Eng., vol. 6, 2009, pp. 11-10.

* cited by examiner

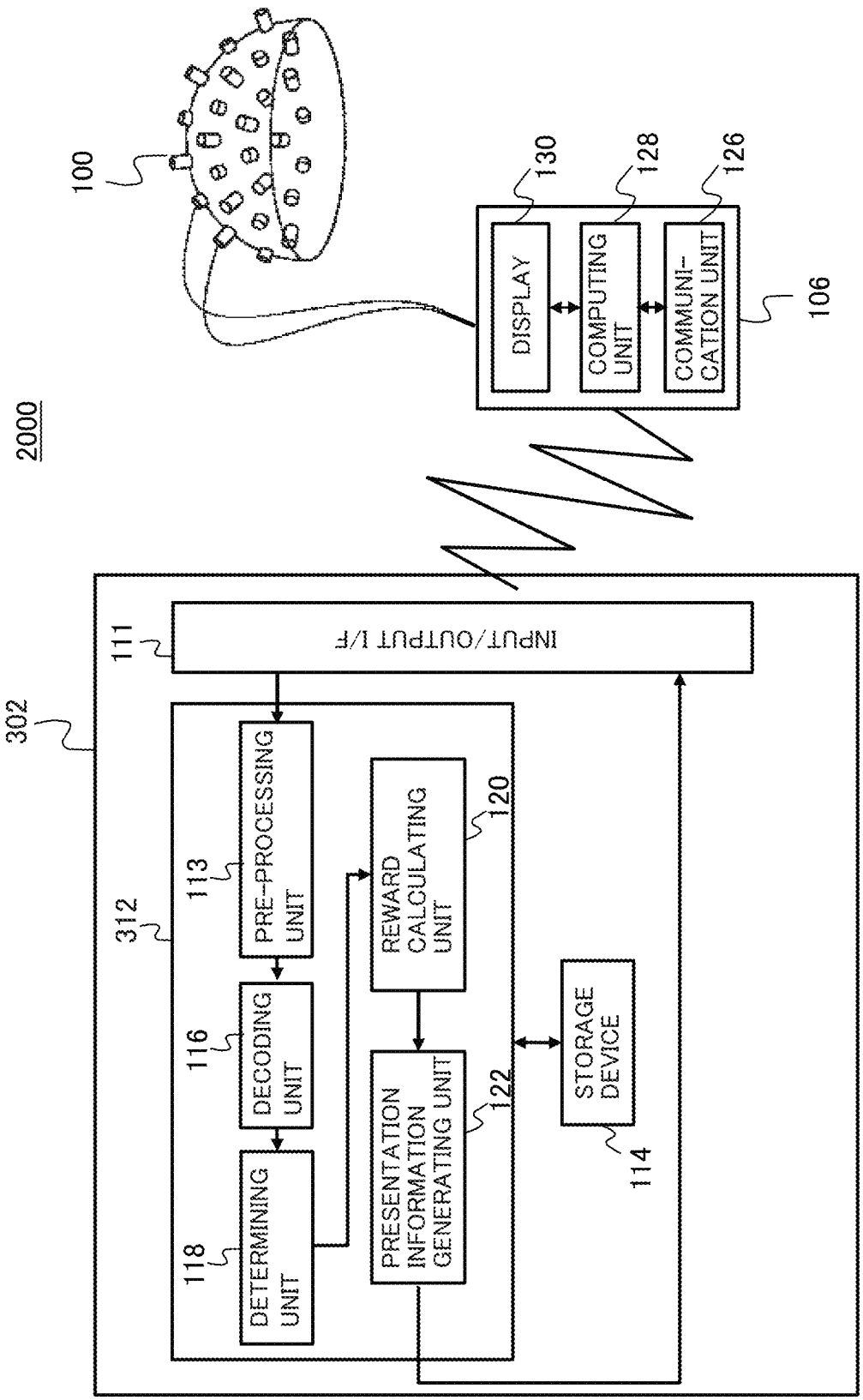

APPARATUS AND METHOD FOR SUPPORTING BRAIN FUNCTION ENHANCEMENT

TECHNICAL FIELD

The present invention relates to apparatus and method for supporting brain function enhancement through learning of an event as an object.

BACKGROUND ART

Recently, training systems for training subjects/trainees utilizing the technology of computer graphics (CG) such as virtual reality (VR) are available. Among such systems, some conduct training while measuring biological reaction of a subject. A training supporting apparatus disclosed in Patent Literature 1 detects, as the biological reaction of the subject, an active region of his/her brain using near infrared light, to assist rehabilitation and image training of a subject with disabilities. Patent Literature 1 is hereby incorporated by reference in its entirety. The training supporting apparatus measures an active region or regions of the subject's brain while the subject is working on a calculation problem or a memory task imposed as a training material; after the end of training, the response of the subject in the training and the record of measured brain activities are studied together to confirm the effectiveness of the training. Patent Literature 2 discloses a training system that always keeps an optimal training scenario in accordance with the biological reaction of a subject during training. Patent Literature 2 is hereby incorporated by reference in its entirety. Patterns of active parts of the brain measured by fNIR (Functional Near Infrared Spectroscopy), fMRI (Functional Magnetic Resonance Imaging), PET (Positron Emission Tomography) or the like are described as the means for measuring biological reaction.

Such a technique of scientifically grasping physiological indexes that would not otherwise be sensed and feeding these back to enable perception by the subject is referred to as "bio-feedback."

Though conventional bio-feedback sometimes utilize biological information such as pulse and breath, it mainly involves human brain wave outputs, converted to visible image or audible sound and output to humans. Through bio-feedback as such, a subject can grasp the state of his/her brain waves on real-time basis. Therefore, bio-feedback is helpful for the subject to control the state of his/her own brain waves.

By way of example, bio-feedback is utilized for treating abnormal cardiac rhythm, headache, autonomic dysregulation and high blood pressure and, in addition, it is utilized for mental training in sports.

As a technique of applying bio-feedback to rehabilitation, Patent Literature 3 discloses a rehabilitation assisting apparatus. The apparatus is for patients suffering from functional impairment or brain dysfunction. The apparatus measures conditions of a rehabilitating patient, and evaluates training contents. The apparatus detects the state of patient's feet using a force sensor or a position sensor, drives thighs, knees and feet joint driving portions to enable coordinated operations of two lower limbs. The apparatus presents the timing of motion of the healthy foot or impaired foot as an image, sound or vibration to the subject, and thereby supports effective gait training.

Operating a switch or a remote controller of electric appliances, for example, is not easy for a physically disabled person. As a solution to this problem, Patent Literature 4 discloses a technique of controlling devices using human brain potential. Patent Literature 4 is hereby incorporated by reference. According to the technique, a control signal for controlling a device is output based on the brain wave obtained from human brain potential. According to the technique, the brain wave is consciously changed using bio-feedback method, and the resulting brain wave is subjected to frequency analysis and arithmetic comparison to obtain the control signal. Another example is disclosed in Patent Literature 5, which is incorporated herein by reference in its entirety. The apparatus disclosed in this reference includes: a detecting unit detecting brain potentials at different portions of a human skull and outputting brain potential data; a pattern generating unit comparing respective detected brain potentials with a prescribed threshold value and generating an activity pattern in accordance with the result of comparison; a pattern database storing in advance the activity patterns representing the state of activation of the brain and control signals for controlling a device in mutually associated manner; and a pattern processing unit comparing the generated activity pattern with the activity patterns in the pattern database, extracting a control signal corresponding to the activity pattern matching the generated activity pattern, and transmitting the control signal to the device. Using this apparatus, it is possible to control the device by brain potential.

Human sensation and perception are ever-changing in accordance with the surrounding environment. Most of the changes occur in a certain early period of human developmental stage, or the period referred to as "critical period." Adults, however, still keep sufficient degree of plasticity of sensory and perceptual systems to adapt to significant changes in surrounding environment. By way of example, Non-Patent Literature 1 reports that adults subjected to a training using specific perceptual stimulus or exposed to specific perceptual stimulus came to have improved performance for the training task or improved sensitivity to the perceptual stimulus, and such results of training were maintained for a few month to a few years. Non-Patent Literature 1 is hereby incorporated by reference in its entirety. Such a change is referred to as perceptual learning, and it has been confirmed that such change occurs in every sensory organ, that is, visual perception, auditory perception, sense of smell, sense of taste, and tactile perception.

The perceptual learning has various specificities, which are believed to come from involvement of lower order visual cortex with the perceptual learning. Further, as reported in Non-Patent Literature 2, there is an unsettled controversy regarding at which stage of visual processing the perceptive learning takes place. Non-Patent Literature 2 is hereby incorporated by reference in its entirety. Thus, it has been unclear what method is effective to support perceptual learning.

Bio-feedback used for perceptual learning needs measurement of brain activity. Various methods therefor have been known, including the following.

A method of measuring electrocorticogram using electrodes placed directly on cerebral cortex.

Non-invasive method of measuring electroencephalogram (EEG), in which small currents generated by activities of neurons in the brain are picked up by electrodes placed on one's skull, amplified and recorded.

Functional MRI (fMRI) visualizing hemodynamic responses related to human and animal brain activities, utilizing Magnetic Resonance Imaging (MRI).

Magnetoencephalography (MEG), which is an imaging technique of measuring with high sensitivity magnetic field generated by electric activities of the brain, using Superconducting Quantum Interference Device (SQUID).

Near-Infrared Spectroscopy (NIRS) measuring increase/decrease of hemoglobin (Hb) or indexes accompanying oxygen exchange information, using infrared light in a non-invasive manner through one's scalp and thereby mapping brain functions.

Conventional studies using fMRI have positively mapped sensory stimulation to humans and brain activities generated in relation therewith. When nerve activities are considered to be codes, the conventional methods try to find how stimuli are represented by the brain, or how the nerve activities encode stimuli.

In contrast, reading what stimuli have been applied from the nerve activities may be called decoding of nerve activities. Decoding of nerve activities is reported in Non-Patent Literature 3, which is hereby incorporated by reference in its entirety.

Besides, Patent Literatures 6 and 7 and Non-Patent Literatures 4 and 5 also report non-invasive measuring methods enabling direct measurement of in-brain nerve activities with high temporal and spatial resolutions from MEG data or EEG data, by utilizing fMRI data. These references are hereby incorporated by reference in their entireties.

Further, Non-Patent Literature 6 reports decoding of brain activities using measurements by electroencephalogram or magnetoencephalography to find that motion activity to a certain orientation among a plurality of orientations is activated, and utilizing the findings to brain-machine interface (BMI, hereinafter "interface" will be denoted as "I/F"). Non-Patent Literature 6 is hereby incorporated by reference.

CITATION LIST

Patent Literature

PTL 1: Japanese Patent Laying-Open No. 2004-294593
PTL2: Japanese Patent Laying-Open No. 2007-264055
PTL3: Japanese Patent Laying-Open No. 2005-13442
PTL4: Japanese Patent Laying-Open No. 2002-125945
PTL5: Japanese Patent Laying-Open No. 2005-278685
PTL6: Pamphlet of PCT International Publication 03/057035
PTL7: Japanese Patent Laying-Open No. 2008-178546

NON PATENT LITERATURE

NPL 1: T. Watanabe, J. E. Nanez Sr, S. Koyama, I. Mukai, J. Liederman and Y. Sasaki: Greater plasticity in lower-level than higher-level visual motion processing in a passive perceptual learning task. Nature Neuroscience, 5, 1003-1009, 2002.
NPL2: Nozomi Ito, Takeo Watanabe, Yuka Sasaki, "Chikaku Gakushu ni okeru Kinnen no Seika" (Recent developments in Perceptual Learning), Vision, Vol. 22, No. 2, pp. 115-121, 2010
NPL3: Miyawaki Y et al. (2009): Visual image reconstruction from human brain activity using a combination of multiscale local image decoders. Neuron. December 10; 60(5):915-29.
NPL4: M. Sato, T. Yoshioka, S. Kajihara, K. Toyama, N. Goda, K. Doya, and M. Kawato, "Hierarchical Bayesian estimation for MEG inverse problem," NeuroImage, vol. 23, pp. 806-826, 2004.
NPL5: T. Yoshioka, K. Toyama, M. Kawato, O. Yamashita, S. Nishina, N. Yamagishi, and M. Sato, "Evaluation of hierarchical Bayesian method through retinotopic brain activities reconstruction from fMRI and MEG signals," NeuroImage, vol. 42, pp. 1397-1413, 2008.
NPL6: Stephan Waldert, Tobias Pistohl, Christoph Braun, Tonio Ball, Ad Aertsen, Carsten Mehring, "A review on directional information in neural signals for brain-machine interfaces", Journal of Physiology—Paris, 103 (2009) pp. 244-254

SUMMARY OF INVENTION

Technical Problem

As described above, however, it has been not necessarily clear how the methods of decoding nerve activities are to be used to enable effective perceptual learning, partly because it is unclear at which stage of brain visual processing the perceptual learning takes place.

Further, it is not necessarily clear either, how to realize BMI or how to implement rehabilitation utilizing the perceptual learning based on the methods of decoding nerve activities.

The present invention was made to solve the above-described problems, and its object is to provide apparatus and method for supporting brain function enhancement enabling enhancement of prescribed brain function through the user's own action, using a method of decoding nerve activities.

Solution to Problem

According to an aspect, the present invention provides an apparatus for supporting brain function enhancement, including: a brain activity detecting device for detecting a signal indicating a brain activity at a prescribed area within a brain of a subject; a storage device storing information of a target activity pattern obtained beforehand with respect to an event as an object of brain function enhancement; and a controller. The controller includes a decoding unit for decoding a pattern of cranial nerve activity from the signal detected by the brain activity detecting device, and a computing unit for computing, based on a result of decoding by the decoding unit, in accordance with degree of similarity of the result of decoding to the target activity pattern, a reward value corresponding to the degree of similarity. The apparatus for supporting brain function enhancement further includes an output device for outputting presentation information representing magnitude of the reward value to the subject.

Preferably, the computing unit outputs, as the presentation information, information for presenting the presentation information corresponding to the reward value to the output device, without presenting the event.

Preferably, the event is an object of perception leading to an identification problem of which class it is classified to in the brain. The decoding unit calculates likelihood of which class the activation pattern of cranial nerve activity corresponds to.

Preferably, the apparatus for supporting brain function enhancement further includes: a supporting terminal including the output device; and a processing device including the decoding unit, the storage device and the computing unit. The supporting terminal includes a communication unit for transmitting a signal detected by the brain function detecting device to the decoding unit.

Preferably, the decoding unit decodes cranial nerve activity of a specific portion, for example, at the early visual areas, of the brain.

Preferably, the brain activity detecting device includes an fMRI device.

Preferably, the brain activity detecting device includes a device for measuring EEG and near infrared light from outside of a skull.

According to another aspect, the present invention provides a method of supporting brain function enhancement, using a decoding device decoding a pattern of cranial nerve activity pattern from a signal from a brain activity detecting device for detecting a signal indicating a brain activity at a specific area within the brain of a subject, including the steps of: decoding, from the signal detected by the brain function detecting device, a cranial nerve activity pattern by means of the decoding device; calculating, in accordance with a degree of similarity between a result of decoding and the target activity pattern obtained beforehand for an event as an object of brain function enhancement, a reward value corresponding to the degree of similarity; and presenting, to the subject, presentation information indicating magnitude of the reward value.

Preferably, at the step of presenting the presentation information, information for presenting the presentation information corresponding to the reward value is output to an output device without presenting the event as the object of brain function enhancement.

Advantageous Effects of Invention

By the apparatus and method for supporting brain function enhancement of the present invention, it becomes possible for the subject himself/herself to take action to enhance his/her brain function, for an event as an object of a prescribed brain function, using the method of decoding nerve activities in the brain.

Further, by the apparatus and method for supporting brain function enhancement, it becomes possible to train a subject on an event as an object of training, using the method of decoding nerve activities in the brain.

Further, by the apparatus and method for supporting brain function enhancement, it becomes unnecessary to apply any stimulus corresponding to the event as the object of training to the subject. Therefore, the training terminal used by the subject can be made small.

BRIEF DESCRIPTION OF DRAWINGS

FIG. 22 is a functional block diagram of a training apparatus 2000 in accordance with a second embodiment.

DESCRIPTION OF EMBODIMENTS

Figure 1:
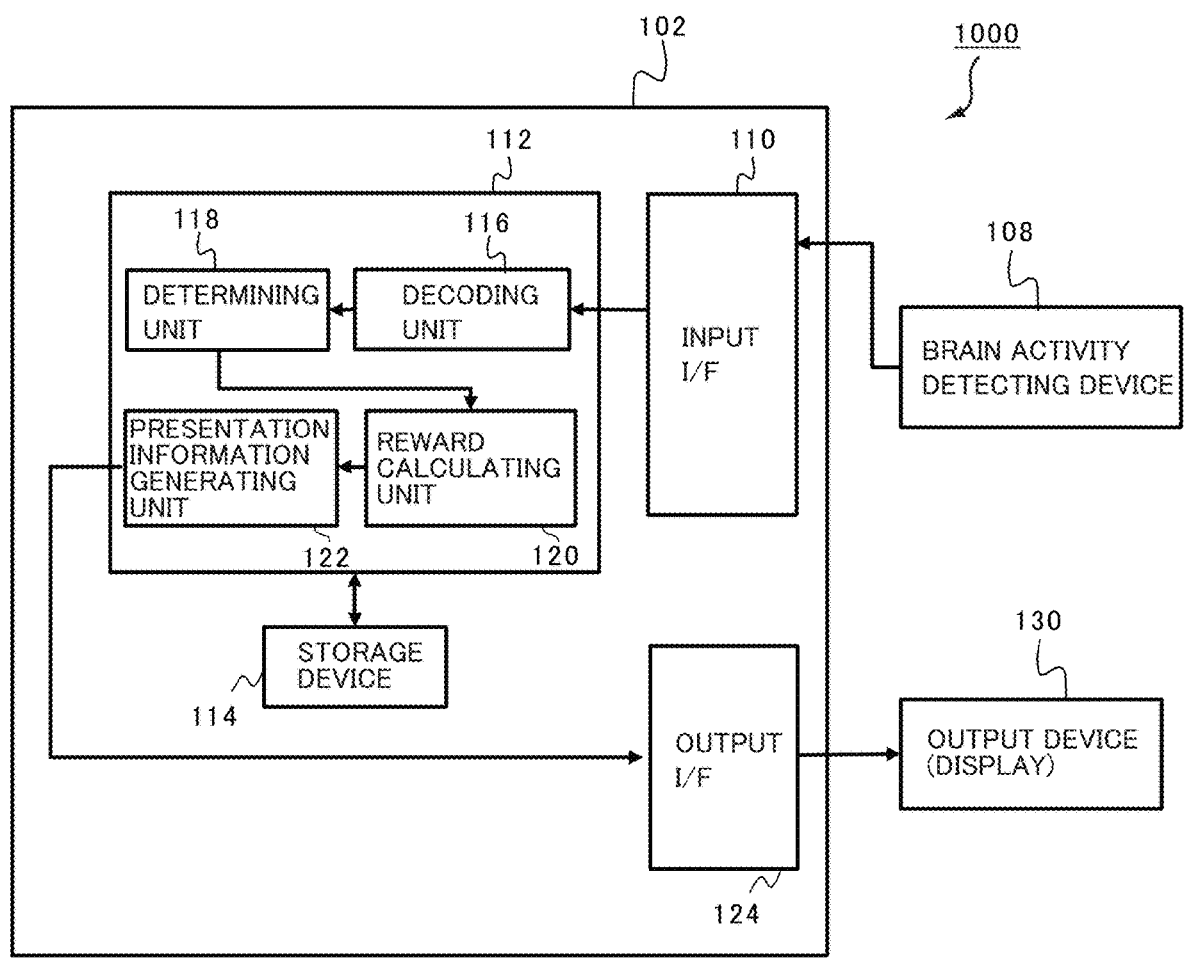
FIG. 1 is a functional block diagram of a training apparatus 1000 in accordance with a first embodiment of the present invention.

In the following, configurations of training apparatuses in accordance with the embodiments of the present invention will be described with reference to the figures. In the embodiments described below, the components and process steps denoted by the same reference characters are the same or corresponding components or steps and, therefore, description thereof will not be repeated unless necessary.

First Embodiment

Referring to FIG. 1, the training apparatus 1000 in accordance with a first embodiment of the present invention includes: a brain activity detecting device 108 for detecting a brain activity in a prescribed area of a brain of a subject (not shown); a processing device 102 receiving and decoding an output from brain activity detecting device 108 and generating information (neurofeedback information) to be presented as a feedback to the subject in accordance with the result of decoding; and a display device 130 receiving an output of processing device 102 and presenting the feedback information to the subject.

As the brain activity-detecting device 108, the fMRI, magnetoencephalography, NIRS, electroencephalogram or a combination of these may be used. Of these, fMRI and NIRS detect signals related to cerebral blood flow change and have high spatial resolutions. Magnetoencephalography and electroencephalogram detect change in electromagnetic field accompanying brain activity and have high temporal resolutions. Therefore, if fMRI and magnetoencephalography are combined, for example, it becomes possible to measure the brain activity with both spatially and temporally high resolutions. Similarly, if NIRS and electroencephalogram are combined, a system of measuring brain activity with high spatial and temporal resolutions can be formed in a small, portable size.

As an output device for presenting the feedback information, here, description will be given assuming a display device 130 used for presenting visual feedback information to the subject. The feedback information, however, is not limited to visual information, and audio information, tactile information or the like may be presented. The output device may be appropriately selected in accordance with the type of information.

Processing device 102 is not specifically limited and, by way of example, it may be realized by a general purpose personal computer. It goes without saying that a dedicated hardware may be used.

Processing device 102 includes: an input I/F 110 for receiving a signal from brain activity detecting device 108; a computing device 112 performing a prescribed computational process on the signal from input I/F 110 for generating presentation information to be presented to the subject; a storage device 114 storing a program for enabling an operation of computing device 112 and information necessary for generating the presentation information mentioned above, and attaining a function of a working memory for the computing device 112; and an output I/F 124 for outputting a signal for displaying the presentation information from computing device 112 to display device 130.

The prescribed computational process executed by computing device 112 includes the following:

Decoding the cranial nerve activity pattern from the signals provided through input I/F 110; calculating similarity between the decoded activity pattern and a target activity pattern obtained beforehand with respect to an event as the object of training; calculating a reward value in accordance with the similarity, based on the calculated similarity; and generating information of target activity pattern, corresponding to the reward value.

Here, the "similarity" may be any of the following:

"Similarity as a pattern" when the pattern of a specific target activity pattern, as a reference obtained beforehand and the pattern of cranial nerve activation at the current time point are output;

Not using the explicit target activity pattern as a reference but using an evaluation value obtained based on predetermined (one or more) evaluation criteria, a result of determination as to how close the pattern of cranial nerve activation at the current time point is to the target; and Regarding which class the cranial nerve activation at the current time point belongs to among a plurality of classes of activity patterns classified in advance, a value representing degree of possibility (for example, likelihood) of the current pattern belonging to the target class.

The computing device 112 includes a decoding unit 116 operating in accordance with a program stored in storage device 114, decoding a signal from brain activity detecting device 108, and deriving to which pattern of activation state of nerve activity receiving what type of stimulus the present brain activity corresponds; a determining unit 118 determining degree of matching of the decoded result decoded by decoding unit 116 with the target activity pattern; a reward calculating unit 120 calculating a reward value in accordance with a function that provides larger value as the degree of matching (similarity) increases, from the result of determination by determining unit 118; and a presentation information generating unit 122 generating presentation information corresponding to the calculated reward value, in accordance with a predetermined method.

Here, visual information is presented as the feedback information. Therefore, presentation information generating unit 122 generates image information representing the magnitude of reward value, as the presentation information. A specific example of the image information will be described later.

What is presented by the display device 130 to the subject is not the visual stimulus itself that causes the pattern of target activation but only the presentation information corresponding to the reward value. Therefore, even when display device 130 is used as the output device of training apparatus 1000, the perception as the object of training is not limited to visual perception. Beside visual perception, auditory perception, sense of smell, sense of taste, or tactile perception may be the object. Further, the information presented by training apparatus 1000 to the subject is not limited to image information and it may be auditory information, smell information, taste information or tactile information, and it may be any information by which the subject can grasp the magnitude of reward value.

In the present embodiment, relation between the presentation information and the magnitude of reward value is selected such that as the magnitude increases, the size of a presented disk increases accordingly. The relation between the magnitude of reward value and the presentation information is not limited to such a relation. In an opposite manner, the size of a presented figure may be made smaller as the reward value increases. Alternatively, the relation between the two may be selected such that as the reward value increases, the figure reaches a specific size. In short, what is necessary is that the presentation information changes as the reward value changes, in accordance with a specific function.

(Perceptual Learning)

In the following, visual stiumuli with respect to orientation, related to the stimuli used in the present embodiment and the perceptual learning thereof will be briefly described.

Figure 2:
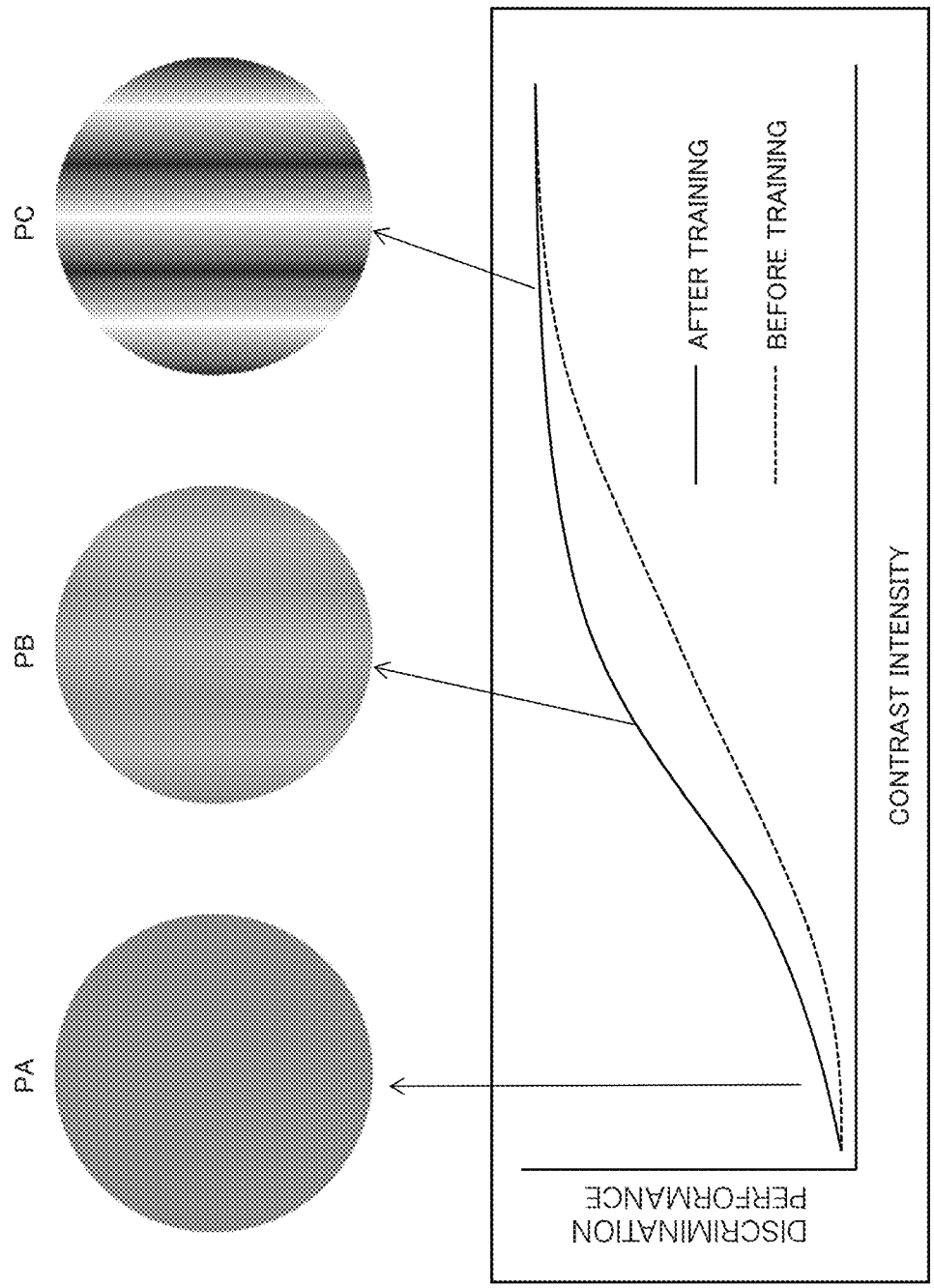
FIG. 2 is a conceptual diagram showing a relation between visual stimuli related to orientation and perceptual learning thereof.

FIG. 2 is a conceptual diagram showing a relation between visual stimuli related to orientation and perceptual learning thereof. In the following, the "visual stimulus related to orientation" means presenting a pattern, which is inclined in a specific orientation, to the subject. As a specific example, a Gabor patch of a specific orientation is presented to the subject.

Here, Gabor patch is one of basic stimulus patterns frequently used in visual science and particularly psychophysical experiments. This is provided by multiplying sinusoidal grating by two-dimensional Gaussian function, and it may be considered to be a part of infinitely continuing sinusoidal grating cutout smooth. Two-dimensional distribution c(x, y) of luminance contrast with the origin being the center will be represented as $$c(x,y)=A \sin(2\pi f_x x) \times \exp(-(x^2/2\delta^2 + y^2/2\delta^2)) \qquad (1)$$

(in the case of vertical grating). Here, A represents amplitude, $f_x$ represents spatial frequency, and variance $\delta$ of Gaussian function is constant regardless of orientation.

FIG. 2 shows, as examples, three patterns PA, PB and PC of figures of vertical gratings with different contrasts, to illustrate the stimulus patterns using Gabor patch. Here, the contrast becomes higher in the order of PA→PB→PC. As an example of perceptual learning, assume a training of subjects to be able to discriminate orientation of gratings even when the contrast of figures is changed.

In general perceptual learning, improved discrimination performance related to contrast intensity is observed after perceptual learning (after training) than before the perceptual learning (before training). This can be confirmed by graphic representation of the two performances, as shown in the lower part of FIG. 2. Here, the discrimination performance can be identified, for example, by gradually adding noise to the Gabor patch images and determining to which level of noise discrimination is possible.

Figure 3:
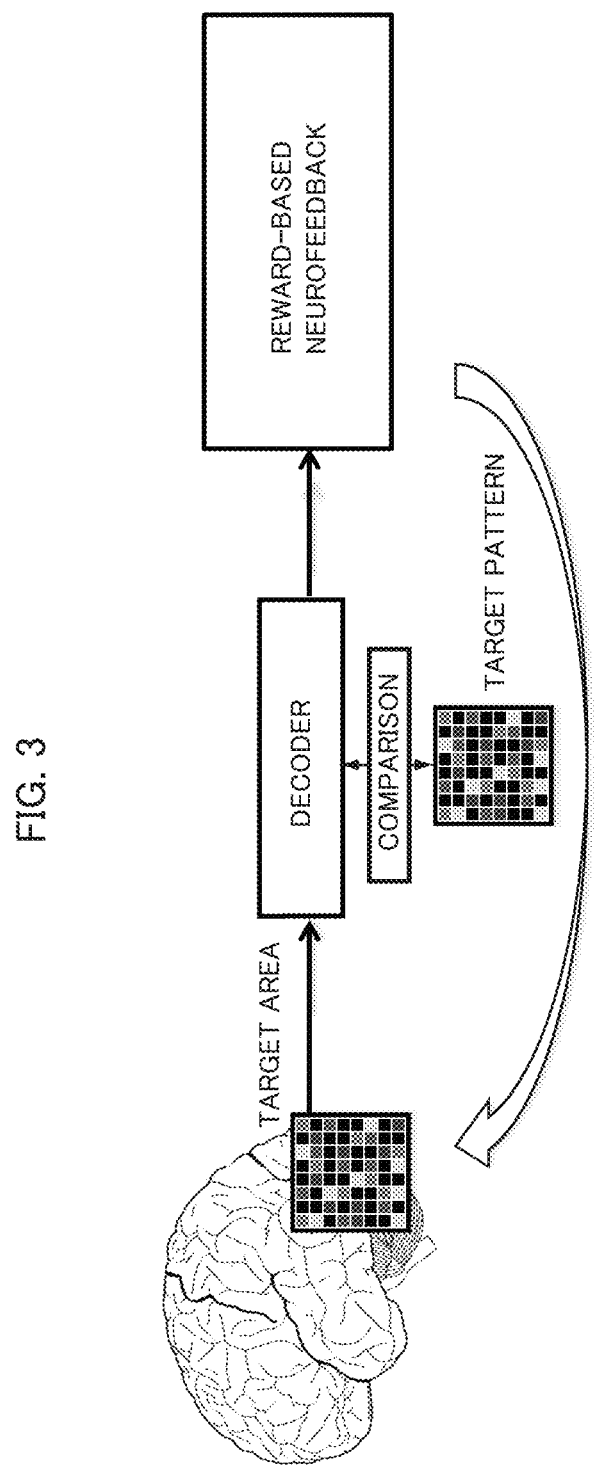
FIG. 3 schematically shows a procedure of perceptual learning of training apparatus 1000 in accordance with the first embodiment.

FIG. 3 schematically shows a procedure of perceptual learning of training apparatus 1000 in accordance with the first embodiment.

As compared with the conventional perceptual learning shown in FIG. 2, training apparatus 1000 of FIG. 1 described above realizes the perceptual learning for the subject in the following manner:

detecting in-brain activity at a prescribed target area of the brain;

decoding signals of detected in-brain activity and thereby obtaining an activity pattern;

comparing the result of decoding with a target activity pattern (target pattern);

obtaining, by computation, reward information in accordance with the degree of matching (similarity) between the two; and neurofeedbacking the visual information in accordance with the reward information to the subject.

Figure 4:
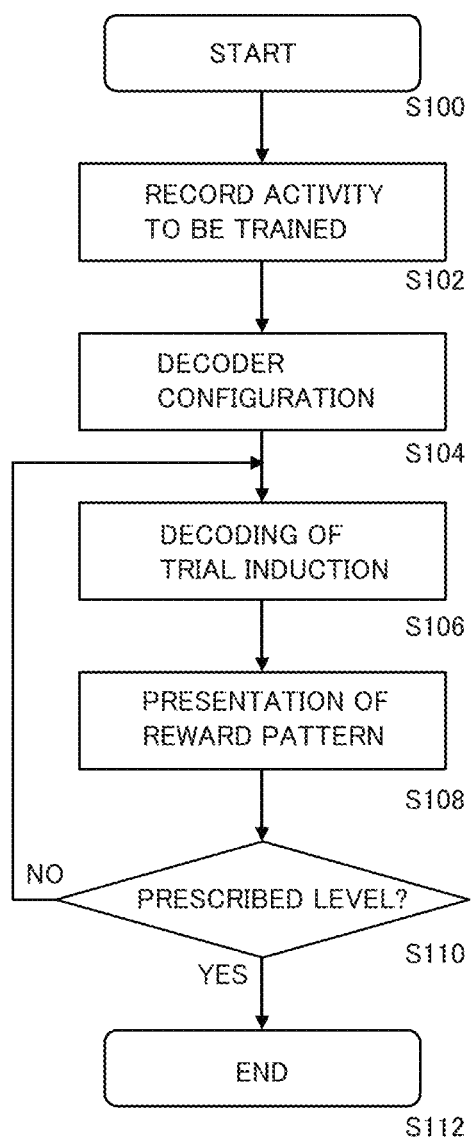
FIG. 4 is a flowchart representing the operation of training apparatus 1000.

FIG. 4 is a flowchart representing the operation of training apparatus 1000.

Referring to FIG. 4, in training apparatus 1000, when the process starts (S100), actions to be trained are recorded for a certain time period (S102), brain activities during such a period of action is detected by brain activity detecting device 108 (FIG. 1), for example, by fMRI, and based on the result of detection, the decoder is trained with respect to the relation between the action and the activity pattern of nerve activities in the brain, whereby training apparatus 1000 configures decoding unit 116 (FIG. 1) (S104). Thereafter, perceptual learning of the subject starts.

In-brain activity pattern evoked and induced by the subject himself/herself is decoded by decoding unit 116 of training apparatus 1000 (S106). Determining unit 118 determines degree of similarity between the result of decoding and a target pattern. In accordance with the result of determination, reward calculating unit 120 calculates the reward value. Presentation information generating unit 122 generates presentation information corresponding to the reward value, and presents it to the subject using display device 130, through output I/F 124 (S108). The subject continues induction of patterns such that the presentation information comes to reflect higher reward value. When the training level reached a prescribed level (S110), the process ends (S112).

By way of example, a reference for determining whether or not the "training level reached a prescribed level" may be that the reward value calculated by reward calculating unit 120 attains to and continuously kept at a defined level of reward value for a prescribed time period. The end of process may be automatically determined by training apparatus 1000, or it may be determined by an administrator of the training.

(Perceptual Learning by Training Apparatus 1000)

In the following, the results of experiments on perceptual learning using training apparatus 1000 will be described.

In the description below, fMRI is used as an example of a method of measuring in-brain activities of the subject.

Though details will be described later, in short, the results of experiment are as follows. The subjects were asked to give efforts to make the size as large as possible of consecutively presented disk shaped figure of a single color. The disk figure represents the presentation information generated in accordance with a prescribed function related to the reward information of the experiment. The size of disk figure was proportional to the likelihood that a temporal fMRI signal activity pattern of early visual areas (first order visual area (V1 area), second order visual area (V2 area)) of the subject is classified as the pattern evoked by the presentation of a real and specific target orientation stimulus. In the present experiment, the size of disk figure refers to the radius of the disk.

The subjects had no knowledge of what the disk figure represented, nor how, exactly, to control its size.

After this procedure, behavioral performance improved significantly for the target stimulus, but not for other orientations.

These results indicate that repetitive induction of a targeted neural activity pattern in the early visual areas of the adult brain is sufficient to cause perceptual learning, without exposure to an external target stimulus, without knowledge of the intention of the experiment.

Figure 5:
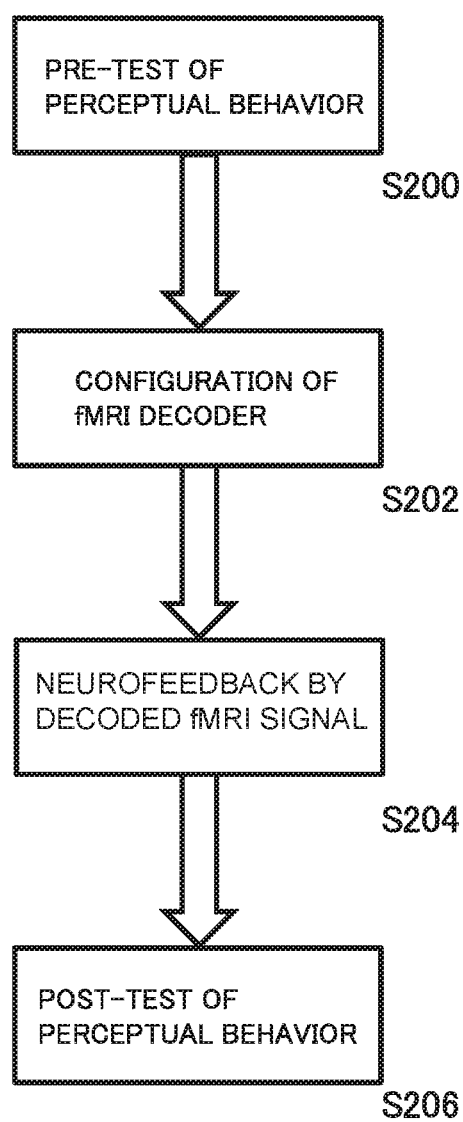
FIG. 5 illustrates a flow of experiment of perceptual learning.

FIG. 5 illustrates a flow of such an experiment of perceptual learning.

First, for the subjects, a pre-test of behavioral performance is conducted (S200). Here, subjects' discrimination performance for the orientation of Gabor patches was measured, to obtain information related to the discrimination performance state before perceptual learning.

Next, subjects were presented with Gabor patches with different orientations, and decoding unit 116 is trained to decode nerve activity patterns in the brain observed by fMRI for the pattern of each patch, whereby an fMRI decoder is configured (S202). Though not limiting, it is assumed that decoding unit 116 utilizes a machine learning algorithm, and through learning, it acquires a function of classifying nerve activity patterns in the brains of subjects to different types of stimuli presented to the subjects while such activation takes place. As the machine learning algorithm, logistic regression, SLR, support vector machine or the like may be available.

Here, Gabor patches are presented to the subjects as stimuli for decoder configuration. In the following, information representing an event as the object of learning will be more generally referred to as stimulus information.

Thereafter, subjects, being monitored by fMRI device, were presented with presentation information corresponding to the reward value to realize neurofeedback and thus perceptual learning is done (S204).

Then, subjects' discrimination performance for the Gabor patches was measured, to obtain information related to the discrimination performance state after perceptual learning (S206).

Details of the flow of FIG. 5 will be described.

The experiment consisted of four stages (S200 to S206) as described above, and the time periods for respective stages are as follows.

i) Pre-test (1 day), ii) fMRI decoder construction (1 day), iii) induction (decoded fMRI neurofeedback, 10 days for six subjects, 5 days for four subjects), iv) post-test (1 day). Different stages were separated by at least 24 hours.

(Pre- and Post-Test Stages)

Figure 6:
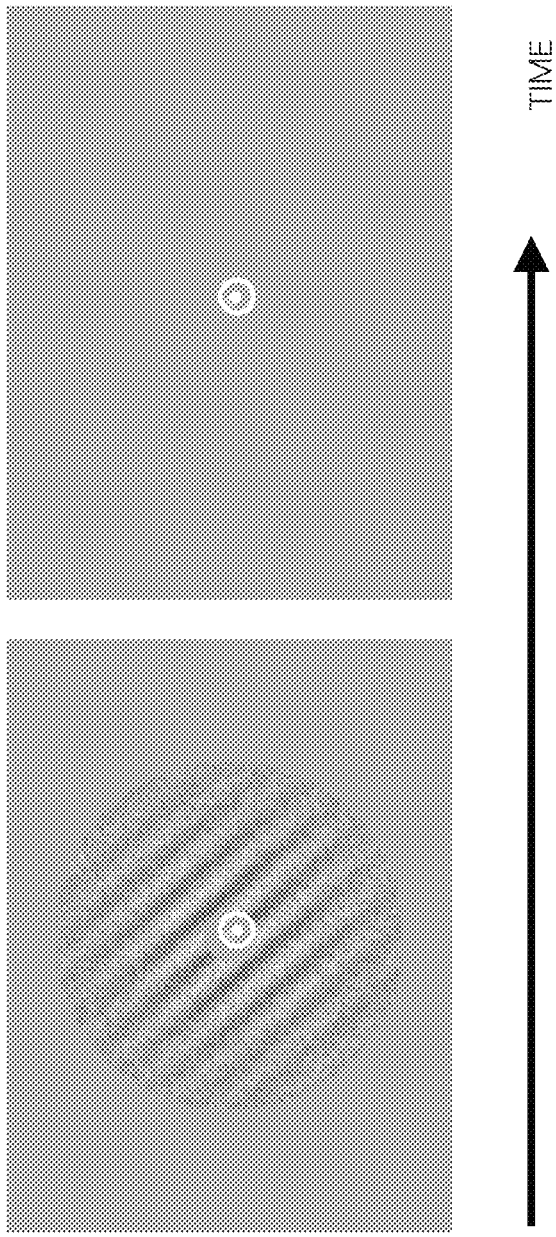
FIG. 6 shows a task imposed on the subjects in pre-test (S200) and post-test (S206).

FIG. 6 shows a task imposed on the subjects in pre-test (S200) and post-test (S206) in the flow of experiment shown in FIG. 5.

In pre-test and post-test stages, to test whether perceptual learning of a target orientation occurred as a result of induction of activity patterns in such early visual areas as V1 and V2, subject' performance in an orientation discrimination task was measured.

As shown in FIG. 6, in each trail, subjects were asked to report which of three orientations (10°, 70° or 130°) had been presented in a Gabor patch.

Figure 7:
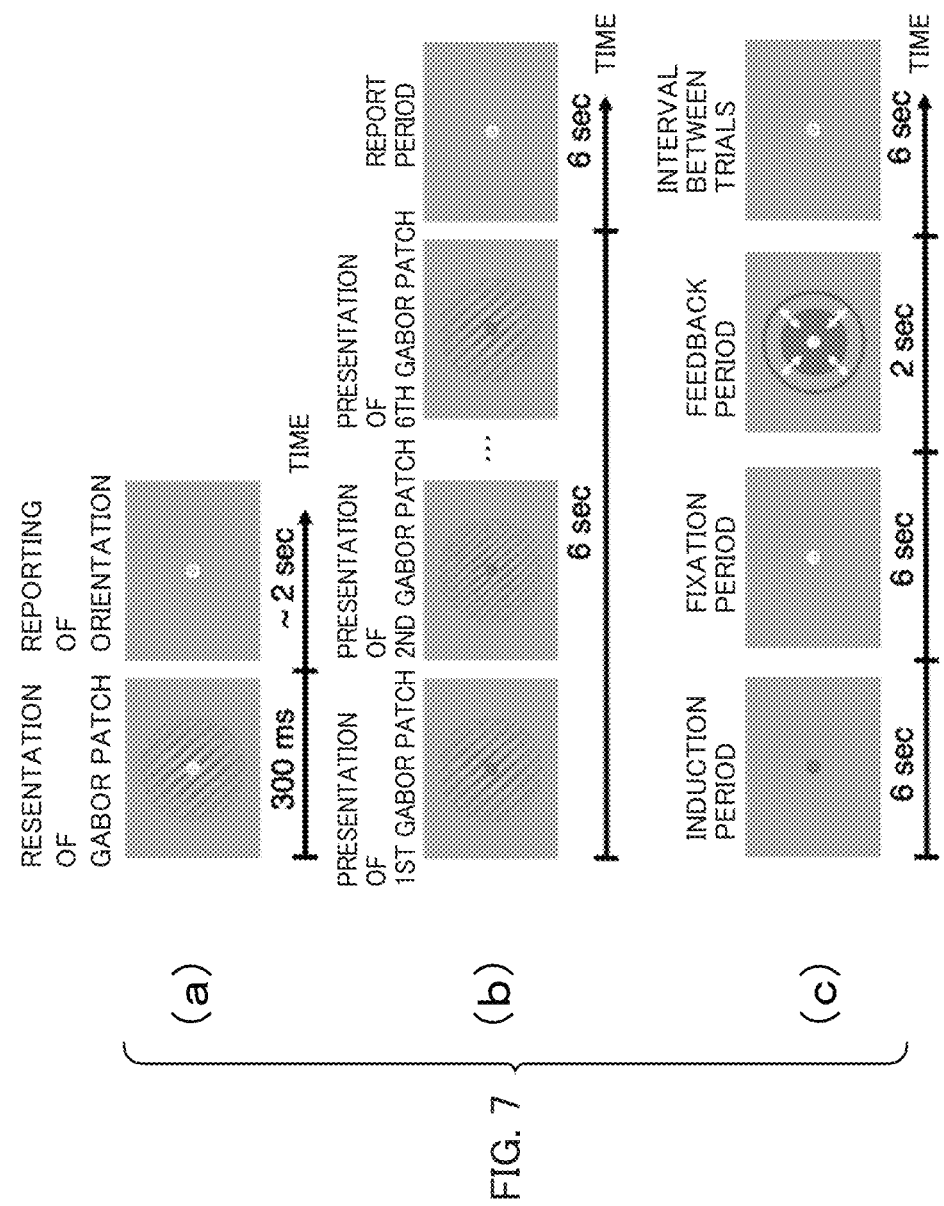
FIG. 7 shows sequences of presenting stimuli to the subjects at various stages of the experiment.

FIG. 7 shows sequences of presenting stimuli to the subjects at various stages of the experiment.

FIG. 7(a) shows sequences of presenting stimulus in the pre-test and post-test stages. First, a Gabor patch was presented to the subjects for 300 ms, after which the subjects were given 2 seconds to report the Gabor orientation they perceived. The presentation and report mentioned above were repeated for a prescribed number of times.

Figure 8:
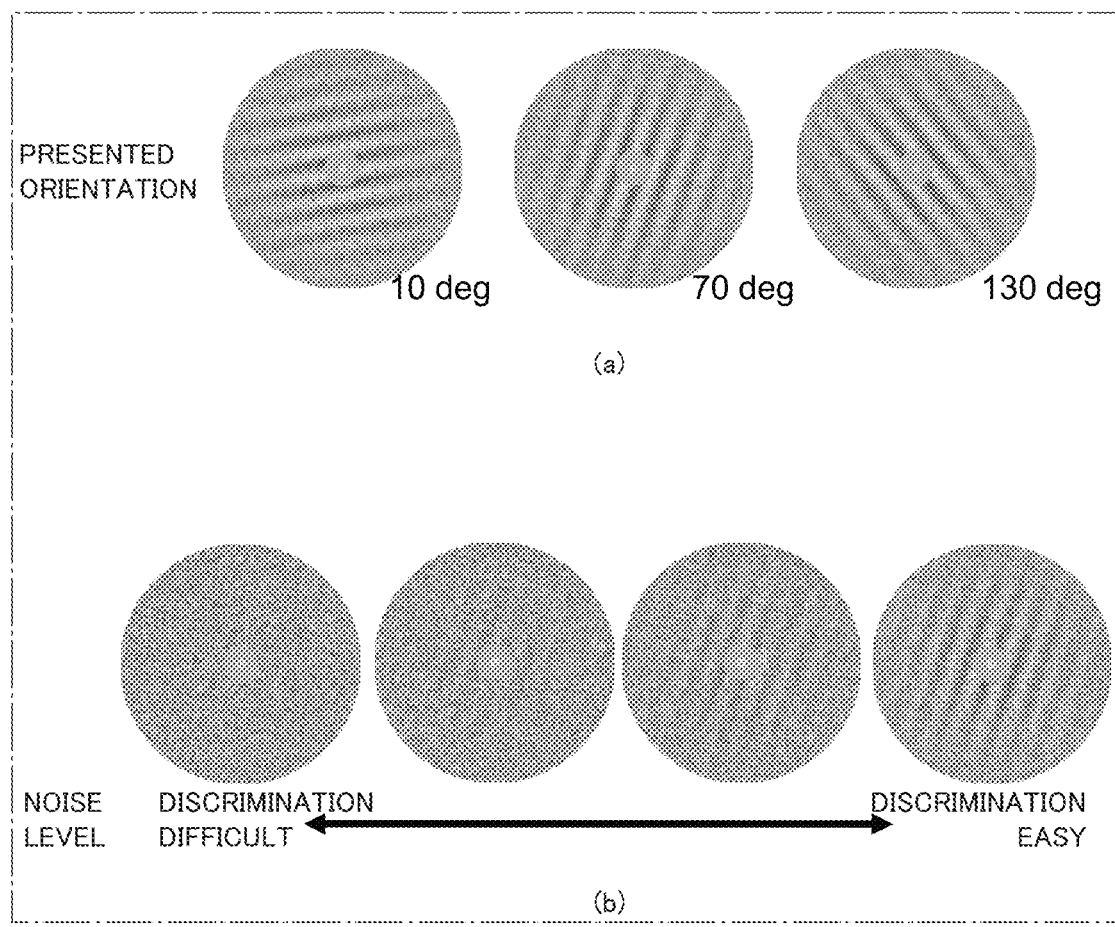
FIG. 8 shows examples of Gabor patches presented as visual stimuli.

FIG. 8 shows examples of presented Gabor patches.

First, the orientation of Gabor patch presented to the subjects is one of 10°, 70° and 130°.

Further, each pattern is presented with different easiness of discrimination, by interposing noise of a plurality of different levels on each pattern.

(fMRI Decoder Configuration Stage)

Next, the fMRI decoder configuration stage (S202) shown in FIG. 5 will be described.

Figure 9:
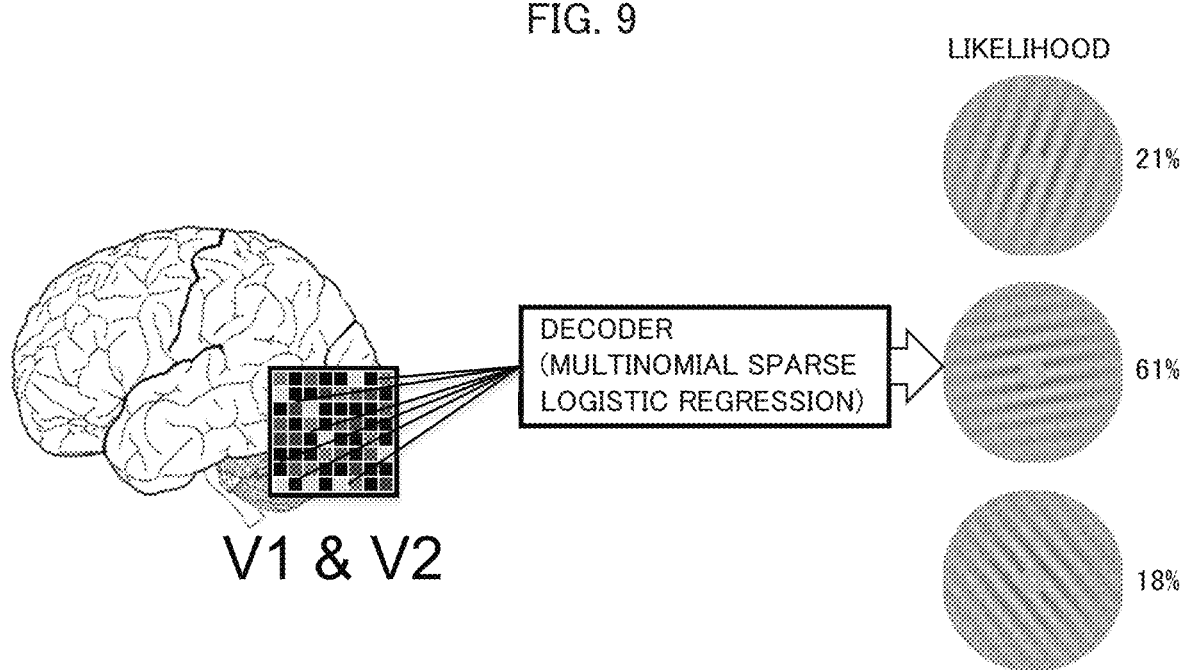
FIG. 9 schematically illustrates the process by the decoder.

FIG. 9 schematically illustrates the process by the decoder.

The decoder configuration stage is executed to obtain fMRI activity patterns from areas V1 and V2 induced by the presentation of each of the three orientations of Gabor patches to each subject.

As shown in FIG. 7(b), the task imposed on the subjects was to maintain fixation on the Gabor patch. Each task trial of the subjects consisted of a stimulus period (6 sec) and a following, response period (6 sec), and 24 such task trials were executed. At the beginning of each stimulus period, the color of the fixation point changed from white to green (in the figures, represented by dark gray; same in the following), to notify the subjects of the start of stimulus period. To each Gabor patch, 50% of noise was added. Further, in the stimulus presentation period, a Gabor patch of one orientation flashed at 1 Hz. One of the three Gabor orientations was randomly assigned to each trial. In 12 trials, that is, half the 24 trials, the spatial frequency of one of the six flashing Gabor patches was increased relative to the other 5 having the same spatial frequency. In the remaining 12 trials, the spatial frequency did not change.

In the response period, no Gabor patch was presented and only the fixation point was presented. In the response period, the subjects were required to respond as to whether there was any spatial frequency change, by pressing a button.

The fMRI signals measured from areas V1 and V2 were converted to activity amplitude in a voxel virtually set in areas V1 and V2. A decoder based on multinomial sparse logistic regression was constructed by machine learning algorithm to classify patterns of the measured fMRI signals to one of the three orientations.

SLR is discussed in Non-Patent Literature 3, Patent Literature 7 and, in addition, in *Brain Communication—Theory and Application—*, SAGARA Kazuhiko, TANAKA Yasuto, TAKEICHI Hiroshige, YAMASHITA Okito, HASEGAWA Ryohei, OKABE Tatsuya, MAEDA Taro, Edited by the Institute of Electronics, Information and Communication Engineers, published by Corona-sha, 1st edition, Apr. 25, 2011, pp. 120-122. This literature is hereby incorporated by reference in its entirety.

Patent Literature 7 mentioned above discloses method and apparatus for predicting behavior, predicting behavior based on brain activity information obtained by such decoding of cranial nerve activities.

In short, SLR is a logistic regression model expanded to Bayesian model, using, as prior distribution of each component of parameter vectors, automatic relevance determination prior distribution, which is a sparse prior distribution. Introduction of sparse prior distribution means that the parameter vectors are limited to sparse vectors (only a few elements have non-zero values and other are 0). SLR prevents over-training by balancing two criteria, that is, "fitting to learning samples" and "sparse parameter representation." In addition, in SLR, by obtaining sparse parameter representation, variable selection takes place simultaneously with parameter learning. Specifically, in the course of learning, of the dimensions of feature vectors, those regarded as unimportant are removed.

In this experiment, inputs to the decoder are ever-changing state of brain activity of the subject, and outputs from the decoder represents calculated likelihood of respective orientations presented to the subject.

Figure 10:
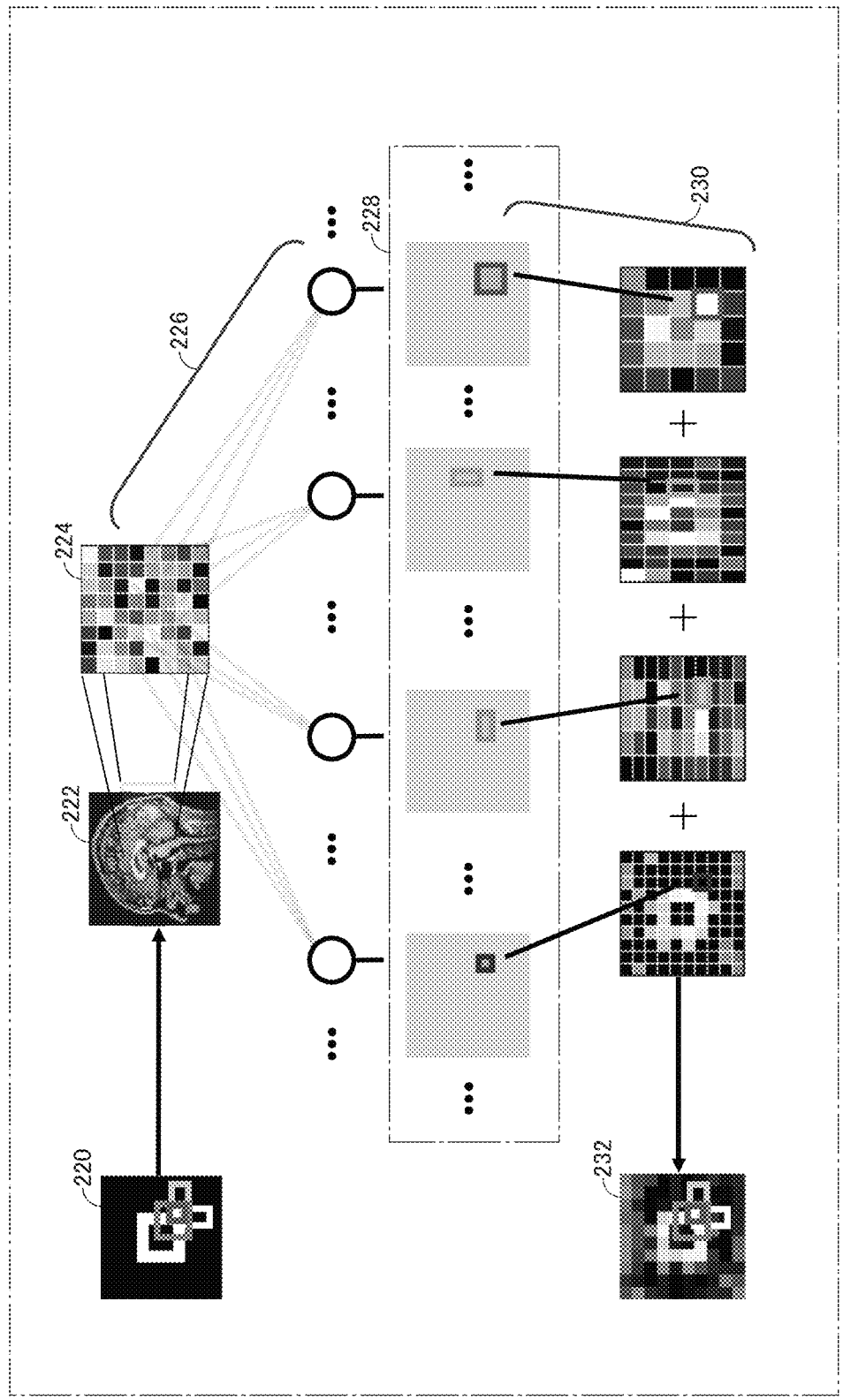
FIG. 10 is a conceptual diagram illustrating a procedure of discriminating an image viewed by a subject using Multinominal Sparse Logistic Regression (hereinafter Sparse Logistic Regression will be referred to as "SLR").

FIG. 10 is a conceptual diagram illustrating a procedure of reconstructing an image viewed by a subject using Multinominal SLR.

A shown in FIG. 10, when a subject 222 views a specific image 220, activity patterns 224 of areas V1 and V2 in the brain of subject 222 are measured as fMRI signals. Based on the measured fMRI signals, contrast prediction 226 is conducted for each small area 228 with multiresolution in the image. Specifically, the fMRI signals are converted to activation amplitudes in the small area 228 with multiresolution, virtually set in areas V1 and V2. Decoding unit 116 realizes learning of a decoder having spatial multiresolution using machine learning algorithm based on multinomial SLR, and by calculating a combination 230 based on linear models thereof, computes a re-constructed image 232.

(Induction Stage: Neurofeedback)

Next, the induction stage of step S204 shown in FIG. 5, that is, the stage of neurofeedback will be described.

Figure 11:
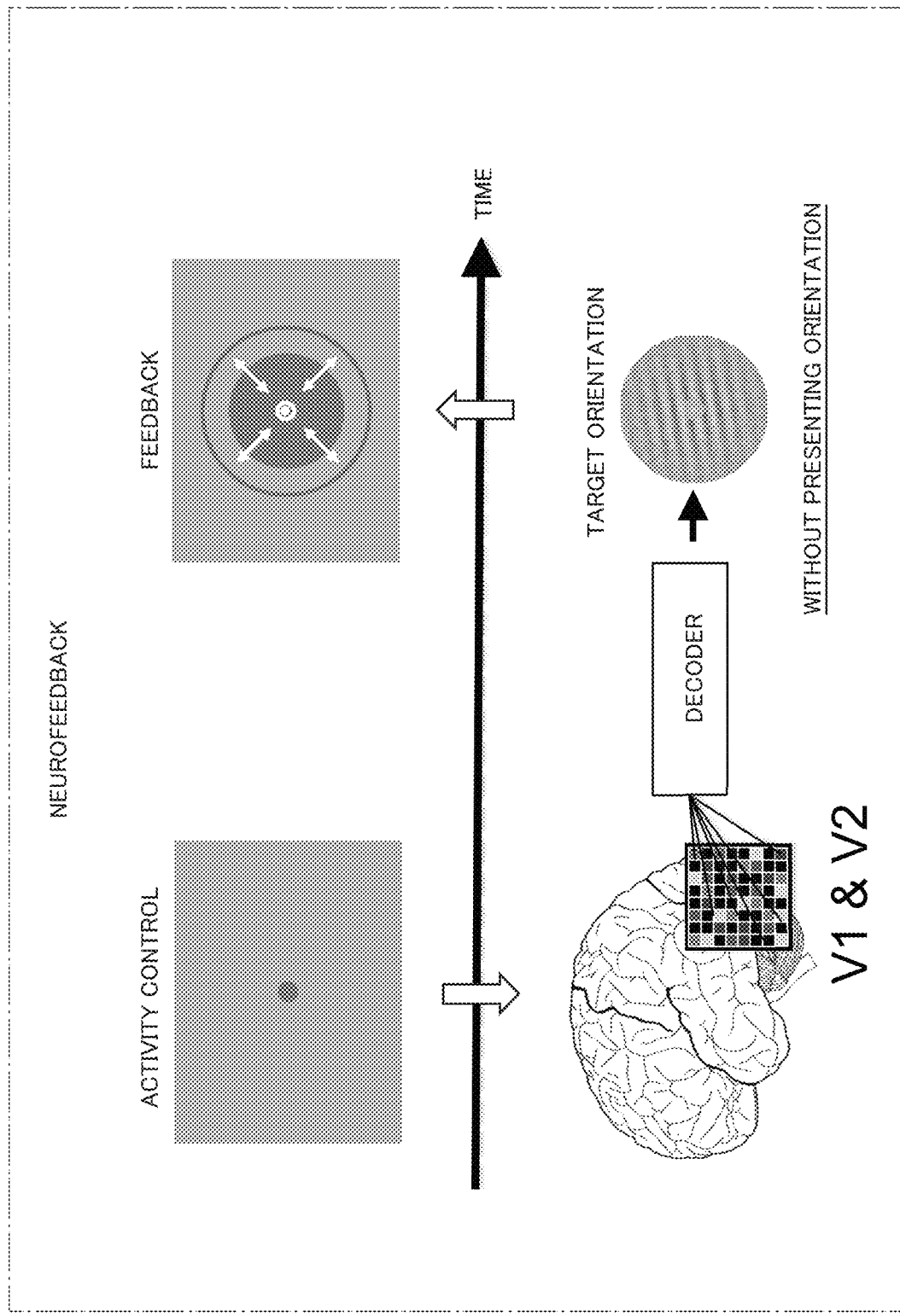
FIG. 11 shows a concept of neurofeedback in training apparatus 1000.

FIG. 11 shows a concept of neurofeedback in training apparatus 1000.

After configuration of decoding unit 116, the subjects took part in the induction stage of 5 days or 10 days. In the induction stage, the subjects learned the method of evoking activity patterns from areas V1 and V2 corresponding to the target orientation.

FIG. 7(c) shows a sequence of the induction stage as such.

As shown in FIGS. 7(c) and 11, during each test trial, the subjects were instructed to regulate the posterior part of their brains, with the goal of making the size of the solid green disc presented 6 seconds later as large as possible (maximum possible size corresponds to the outer circumference of the green disk).

The size of the disc presented in the feedback period corresponded to the decoder output with respect to the target orientation. The decoder output represents the magnitude of likelihood of BOLD (Blood Oxygenation Level Dependent) signal in areas V1 and V2 classified to the target orientation.

Specifically, the disk size represents how much the pattern obtained from the fMRI signal in the induction period corresponded to the pattern induced by the real targeted Gabor patch orientation presented through the above-mentioned fMRI decoder configuration stage (similarity).

The subjects, however, were not informed of what the size represented. The subjects were told that they would receive a payment bonus proportional to the mean size of the feedback disc.

Figure 12:
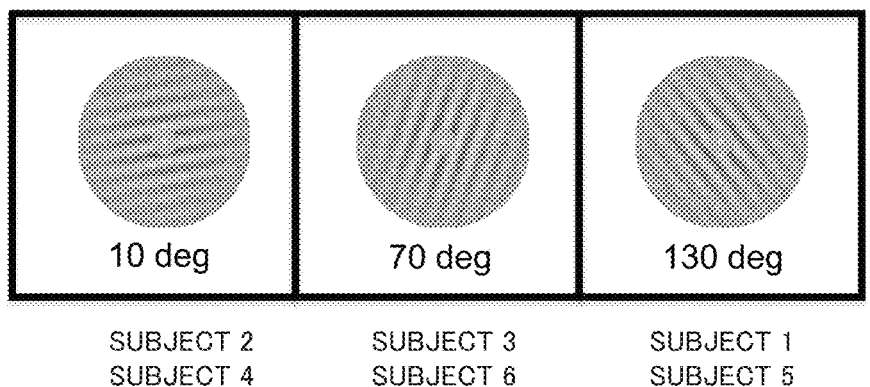
FIG. 12 shows orientations as targets, allocated to each subject.

FIG. 12 shows orientations as targets, allocated to each subject.

The subjects, however, were not informed of which orientation is his/her target orientation.

Note that all other information, including the target orientation, the purpose of the neurofeedback, and the meaning of the disc size, was withheld from the subject. (Activation Patterns of In-Brain Activities Learned by the Subjects in the Induction Stage)

Actual presentation of the target orientation evokes an activity pattern in the neurons of areas V1 and V2 of the subject's brain. In the following, whether the subjects could learn to induce an activity pattern corresponding to the activity pattern by him/her without any presentation of the target orientation will be examined.

To test whether subjects could induce the neural activity patterns, during the induction stage, first, the following test was conducted. First, for each subject, a target orientation and two other orientations rotated by ±60° from the target orientation were determined. We examined whether outputs of the decoder could be biased toward the selected target orientation by the subject, compared with the other two orientations.

Figure 13:
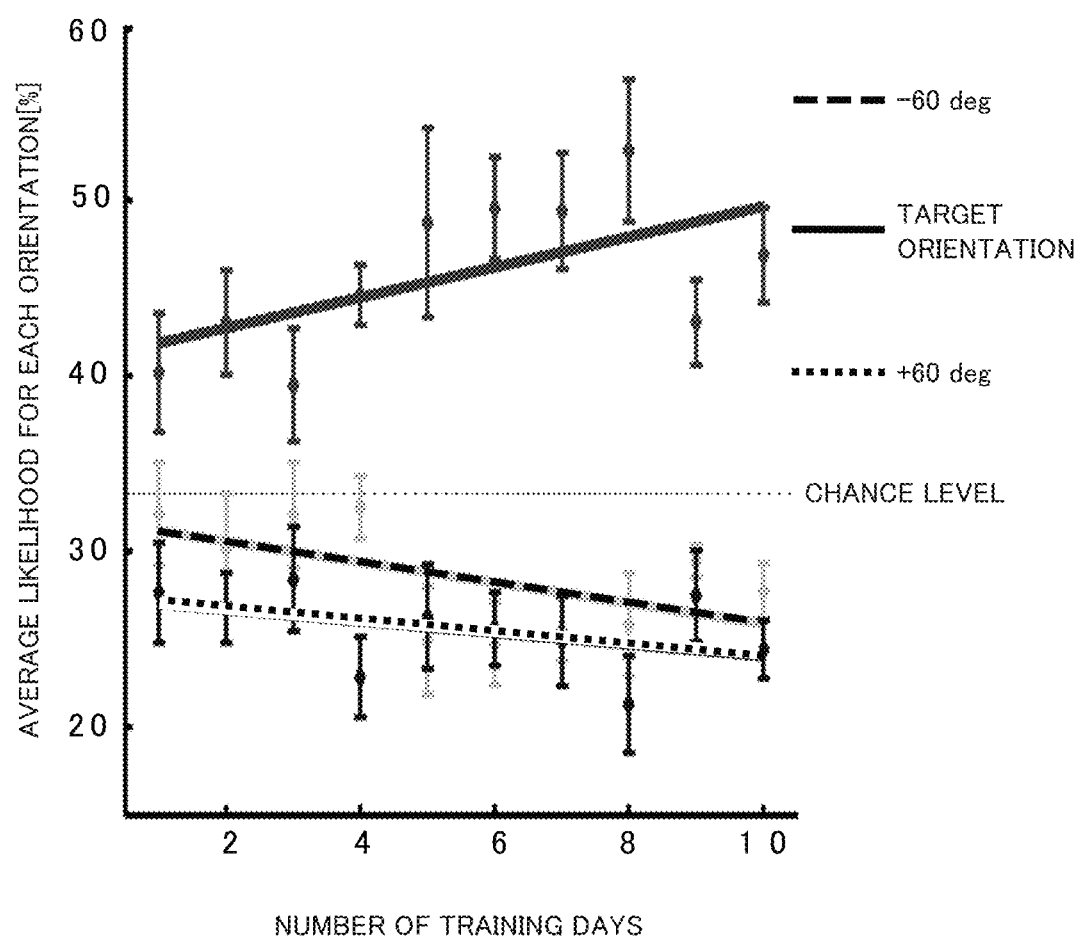
FIG. 13 shows average likelihood of each of three orientations (different by 60 degrees from each other) evaluated by the decoder in the induction stage.

FIG. 13 shows average likelihood of each of three orientations (different by 60 degrees from each other) evaluated by the decoder in the induction stage.

The overall mean likelihood of the target orientation in the decoder output for areas V1 and V2 was significantly higher than chance across the subjects on average during the induction stage (result of t-test:t(9)=3.34, $P<10^{-2}$).

These results indicate that the subjects could induce activity patterns (in areas V1 and V2) that closely corresponded to the activity pattern evoked by the target orientation and are distinguishable from the activity patterns evoked by the other orientations in areas V1 and V2.

Figure 14:
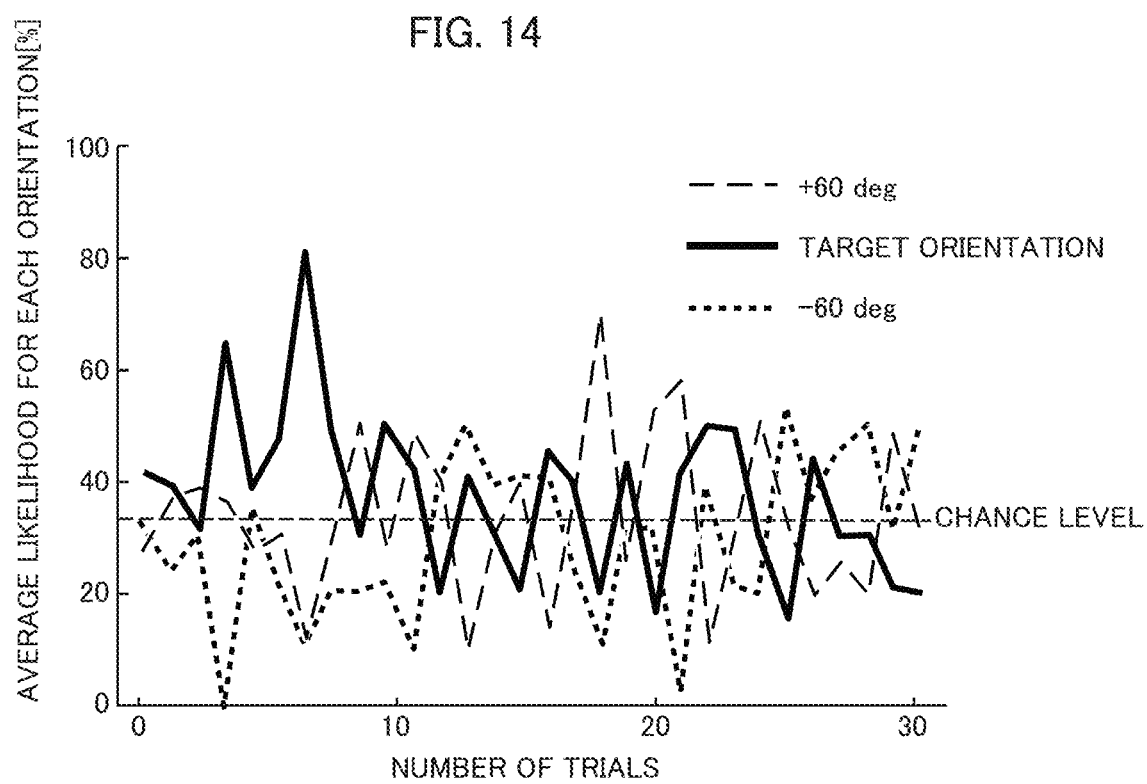
FIG. 14 shows average likelihood among subjects with respect to the target orientation, for the first stage test of day 1 of neurofeedback.

FIG. 14 shows average likelihood among subjects with respect to the target orientation, for the first stage test of day 1 of neurofeedback.

As can be seen from FIG. 14, the mean likelihood across the subjects of the target orientation for the first 30 trials was around chance level.

From the comparison between FIGS. 13 and 14, it can be seen that there was no significant orientation bias for the target orientation before neurofeedback, and that subjects quickly learned to induce activity patterns matching the target orientation even during the first neurofeedback day.

Figure 15:
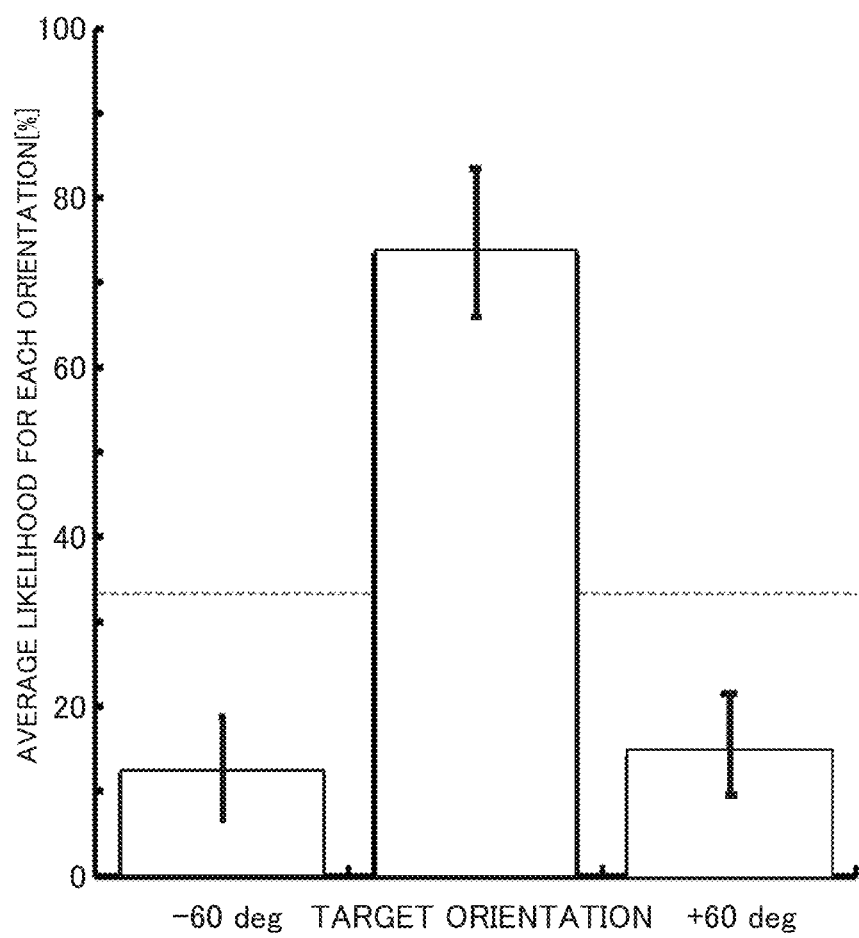
FIG. 15 shows average likelihood for the three orientations calculated by the decoder from average activity patterns for the entire induction stage, in areas V1 and V2.

FIG. 15 shows average likelihood for the three orientations calculated by the decoder from average activity patterns for the entire induction stage, in areas V1 and V2.

In FIG. 15, to further confirm that subjects could induce the neural activity patterns, the same decoder was applied to the overall mean activation pattern, rather than trial-by-trial activation patterns, in areas V1 and V2 during the induction stage for each subject.

Consistent with the results of trial-by-trial decoding, the mean likelihood of the target orientation was significantly higher than chance (result of t-test:t(9)=2.69, P=0.02).

This result further supports that, during the induction stage, subjects could learn to consistently induce a neural activity pattern in areas V1 and V2 that corresponded to the activity pattern evoked by the presentation of the target orientation.

(Were the Subjects Aware of the Purpose of the Induction Stage?)

After the post-test stage, subjects were asked about what they thought the size of the feedback disc represented. None of their responses was even remotely related to the true workings of the experiment.

Then, after being told that the disc size represented the possibility of one of three orientations, subjects were asked to report the orientation they thought they had been trained on. Only 3 out of 10 subjects correctly chose her/his target orientation. The percentage of the choices of the target orientation was statistically undistinguishable from what would be expected from chance (Chi-square test, $x^2$=0.20, P=0.90). These results suggest that the subjects were aware neither of the purpose of the induction stage nor the orientation corresponding to the induced pattern of neural activity.

The purpose of the induction stage was to have subjects learn and then continue to induce activity patterns that corresponded to the neural activity pattern in V1 and V2 evoked by the presentation of a target orientation at the decoder construction stage.

As previously mentioned, the results indicate that on the first day of the induction stage, the subjects already learned to induce activity patterns that were classified as the target orientation more frequently than as the other two orientations. Further, this tendency became stronger as neurofeedback trials progressed.

(Improvement of Discrimination Performance Through Perceptual Learning)

Figure 16:
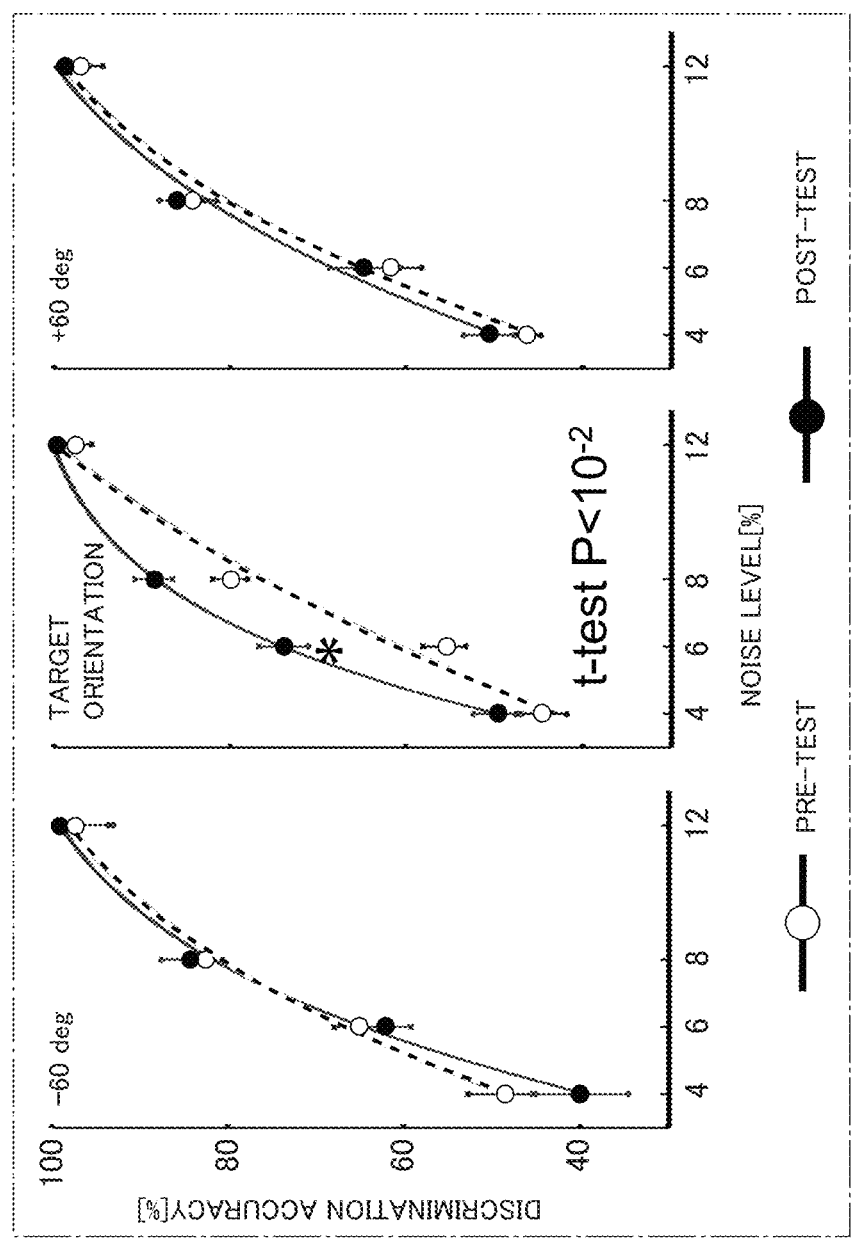
FIG. 16 compares discrimination performance of visual stimuli in pre-test and post-test.

FIG. 16 compares discrimination performance of visual stimuli in pre-test and post-test.

Three-way (test stage×orientation×S/N ratio) analysis of variance with repeated measures indicated significant main effect of S/N ratio (F(3, 27)=683.17, $P<10^4$) and significant effect of interaction between test stage, orientation, and S/N ratio (F(6, 54)=2.68, P=0.02).

Figure 17:
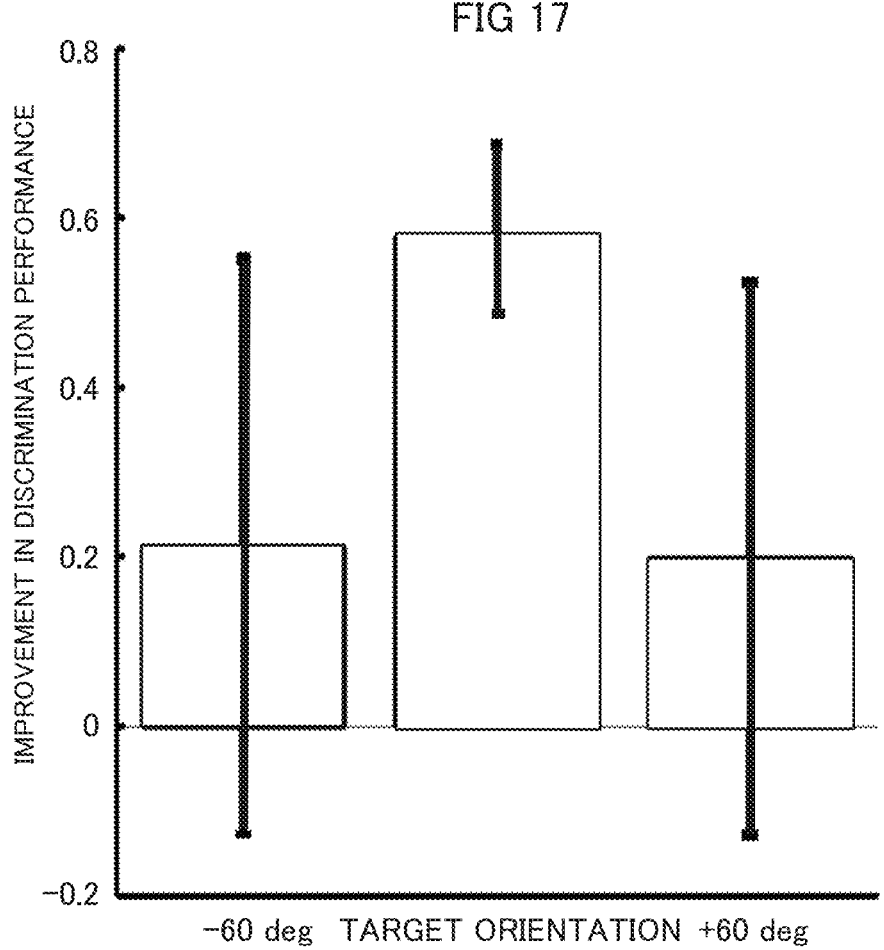
FIG. 17 represents improvement d' in discrimination sensitivity, as the difference between the post-test and pre-test.

FIG. 17 represents improvement d' in discrimination sensitivity, as the difference between the post-test and pre-test.

Post-hoc t-test between accuracies in pre- and post-tests revealed that discrimination performance for the target orientation significantly improved at the 6% S/N ratio (t(9)=5.76, $P<10^{-2}$ with Bonferroni correction by 12 comparisons).

Improvement in discrimination sensitivity d' in the pre-test subtracted from that of the post-test was significantly greater than zero for the target orientation at the 6% S/N ratio (t(9)=5.60, $P<10^{-3}$ with Bonferroni correction by 3 comparisons).

From these results, we conclude that mere repetitive induction of the activity patterns corresponding to activity patterns in areas V1 and V2 evoked by the presentation of a target orientation caused the activity patterns in the subjects, without presenting the pattern. In other words, the subjects has accomplished perceptual learning specific to the orientation.

(Relationship Between the Likelihood of the Target Orientation in V1 and V2 and Sensitivity (d') Changes)

Figure 18:
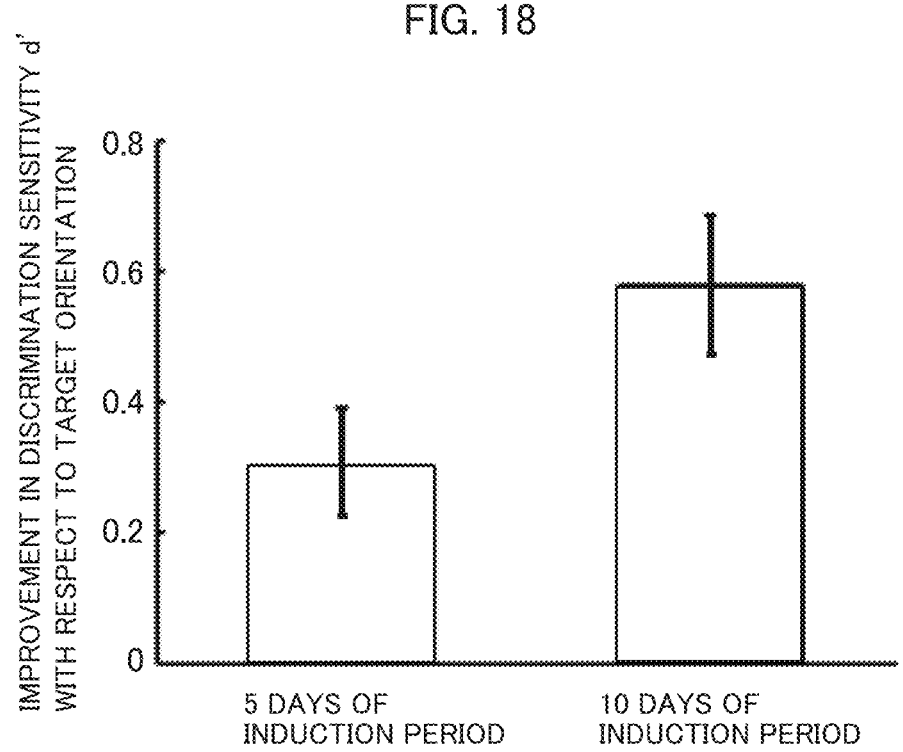
FIG. 18 shows a relation between the number of days of induction stage and the improvement d' in discrimination sensitivity.

FIG. 18 shows a relation between the number of days of induction stage and the improvement d' in discrimination sensitivity.

The sensitivity changes for the subjects with 10 days training (induction) were larger than that with 5 days training. The results were consistent with the general tendency that the magnitude of perceptual learning is larger with longer training until it reaches an asymptote.

Figure 19:
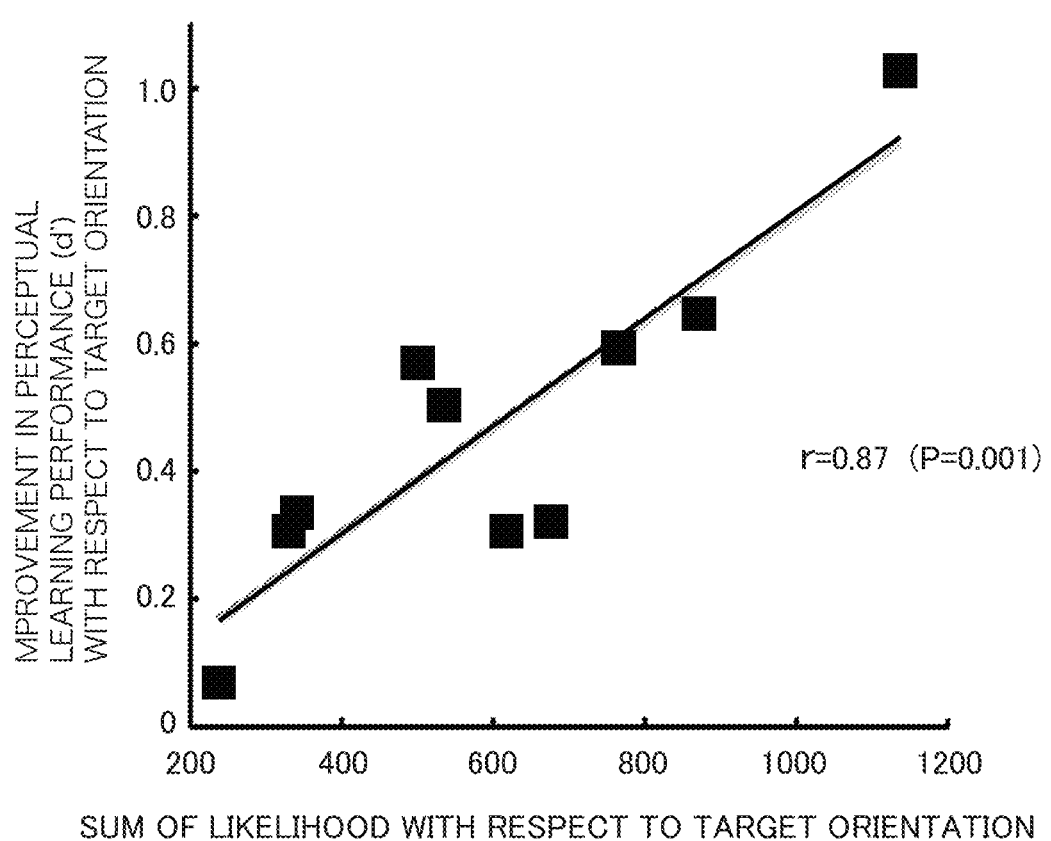
FIG. 19 plots variation in sensitivity with respect to summation, with the summation of target orientation likelihood calculated for every trial of every subject.

FIG. 19 plots variation in sensitivity with respect to summation, with the summation of target orientation likelihood calculated for every trial of every subject.

The correlation was even stronger for the likelihood summation ($r=0.87$, $P=10^{-3}$) than the average likelihoods ($r=0.74$, $P=0.01$).

These results indicate that the closer the pattern that the fMRI neurofeedback induced was to that of the pattern evoked by the actual presentation of the target orientation and the longer the training was, the larger the magnitude of performance improvement after training.

Figure 20:
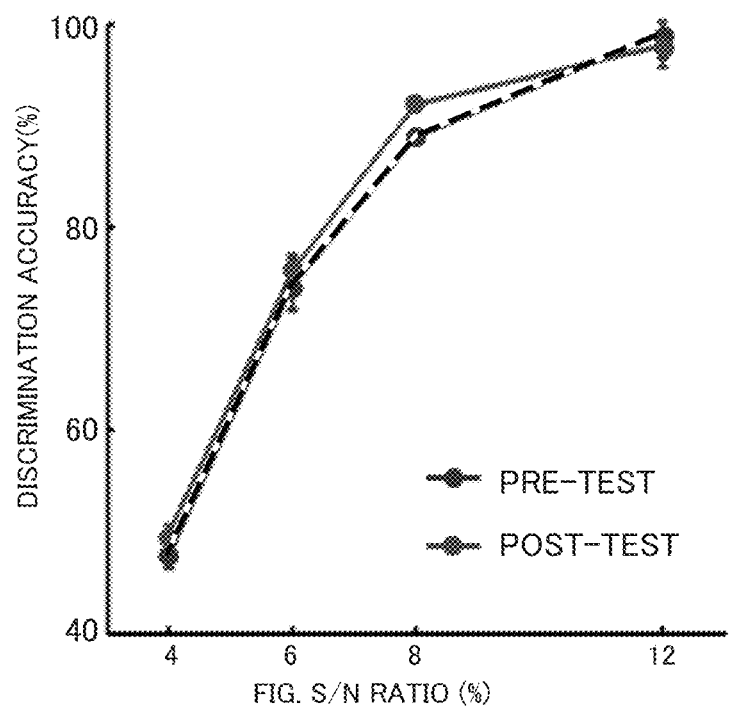
FIG. 20 shows results of control experiment by six new subjects.

FIG. 20 shows results of control experiment by six new subjects.

To test whether the perceptual learning observed in the main experiment resulted simply from subjects' participation in the test stages, we conducted a control experiment with 6 new subjects. For these subjects, only the pre- and post-test stages were conducted without the induction stage. The time interval between the pre- and post-tests was identical to the mean time interval in the main experiment.

As shown in FIG. 20, no significant performance improvement was observed, indicating that the perceptual learning in the main experiment was not due merely to the effects of the test stages.

Though the subjects were asked to discriminate three orientations in the description above, naturally, the number is not limited to three, and larger number of orientations may be used. The visual information as the object of discrimination is not limited to orientation as described above. Other visual stimulus to which neurons in the early visual areas respond, such as spatial frequency or color may be available. The object to be discriminated by the subjects is not necessarily limited to visual information, and more generally, it may be any object "that can lead to the identification problem of to which class it is classified."

As described above, by the training apparatus in accordance with the present embodiment, perceptual training using the method of decoding nerve activity can be realized without presenting specific stimulus information to the subjects.

As described above, it is confirmed that the perceptual learning itself occurs in every sensory organ, that is, visual perception, auditory perception, sense of smell, sense of taste, and tactile perception. Therefore, applications of training apparatus 100 may include the following.

i) Relaxation Training

Relaxation training refers to training for decreasing sensitivity to tension or to feeling of anxiety, so as to alleviate hyper tension or competition anxiety one suffers from immediately before the start of sport competition. In-brain activity of the competitor in mentally relaxed state and the state of in-brain activity during training are compared by training apparatus 1000, and the degree of matching with the relaxed state is fed back as the feedback information to the competitor, whereby relaxation training of the competitor by training apparatus 1000 can be executed.

The usage of such relaxation is not limited to sports training. Generally, in normal life, training using training apparatus 1000 may be conducted to realize deeper relaxation of the user at the time for rest.

ii) Image Training

Image training refers to a method of alleviating stage fright during a competition and keeping concentration, in which a competitor images visual images and muscle movements as real as possible assuming an exercise or a game scene, and he/she simulates the flow of the game or the atmosphere of the venue beforehand.

Image training in this sense has already been utilized by actual athletes as mental training to realize one's potential in a relaxed state on a real stage.

Here, provided that "the state of brain activity in which the subject is under tension for the competition in the real part but simultaneously not too serious" has been acquired as data beforehand, it is possible to execute the mental training on the subject using training apparatus 1000, with the degree of matching between the state of in-brain activity as such and the in-brain activity during the training fed back as the feedback information.

Image training has been used for subsidiary practice to master motor skills. By way of example, the state of in-brain activity when a subject hits a beautiful shot on a golf course may be obtained as data beforehand; the degree of matching with the in-brain activity of the subject during training may be measured by training apparatus 1000; and the results may be fed back to the subject as the feedback information. In this manner, mental training for mastering motor skills can be executed using training apparatus 1000.

iii) Treatment of Disease Resulting from Brain Function

When a part of brain function of a patient suffering, for example, from mood disorder such as depression or dementia tends to decline, currently, it is possible to suppress the symptom or to slow the progression of the disease to some extent by medication. If data of the state of in-brain activity when the patient is in a desirable condition could be obtained beforehand, training of the patient using training apparatus 1000 would be effective to improve the condition of the patient.

It is known that, when a part of the brain is damaged, for example, by an injury, other part of the brain possibly acts to compensate for the damaged portion. By measuring the in-brain activity of the subject in such compensation stage and feeding back the results, training apparatus 1000 may possibly be used as a method of rehabilitation.

iv) Training of Sense of Smell, Sense of Taste and Tactile Perception

Generally, it is difficult to artificially create stimulus for training sense of smell, sense of taste and tactile perception. Training apparatus 1000 after configuration, however, does not require artificial creation of such stimulus. Therefore, training on the subject is possible with respect to these sensory organs.

v) Improvement of Memory Retention

It is reported that external stimulus of a certain frequency during non-REM sleep is effective for memory consolidation, in Lisa Marshall, Halla Helgadottir, Matthias Molle, Jan Born, "Boosting slow oscillations during sleep potentiates memory", Nature, Vol. 444, 30 Nov. 2006, pp. 610-613.

According to this report, external stimulus has an influence on the activation of a portion of the brain related to memory consolidation. In other words, if the state of activity of that portion which is activated were obtained as data and any reward could somehow be given to the sleeping subject, training apparatus 1000 could be used as an apparatus assisting memory consolidation during sleep. As the reward in such a situation, by way of example, if the subject is in a desirable state, fine fragrance may be given to the subject and if the subject is in an undesirable state, weak mechanical or electric unpleasant stimulus may be given to the subject.

In training apparatus 1000, what is presented by display device 130 to the subject (trainee) is not the stimulus information itself that generates the pattern of target activation. What is presented is absolutely the presentation information corresponding to the reward value. It is unnecessary for the subject to be aware of the event itself as the object of learning. Therefore, even if the event as the object of learning is what the subject despises or what he/she wants to stay away before learning, learning of such an object is still possible. By way of example, assume that one has a "phobia (phobic disorder)" that produces intense fear of a specific thing as to cause inconvenience in daily life or social activity. Training apparatus 1000 can be used for training to alleviate such symptom.

As described above, training apparatus 1000 is capable of "training" of brain function and, more generally, capable of supporting enhancement of brain function. In this sense, the apparatus that can realize procedures as described above will be referred to as an "apparatus for supporting brain function enhancement."

Second Embodiment

In the following, a configuration of the training apparatus in accordance with the second embodiment will be described.

Figure 21:
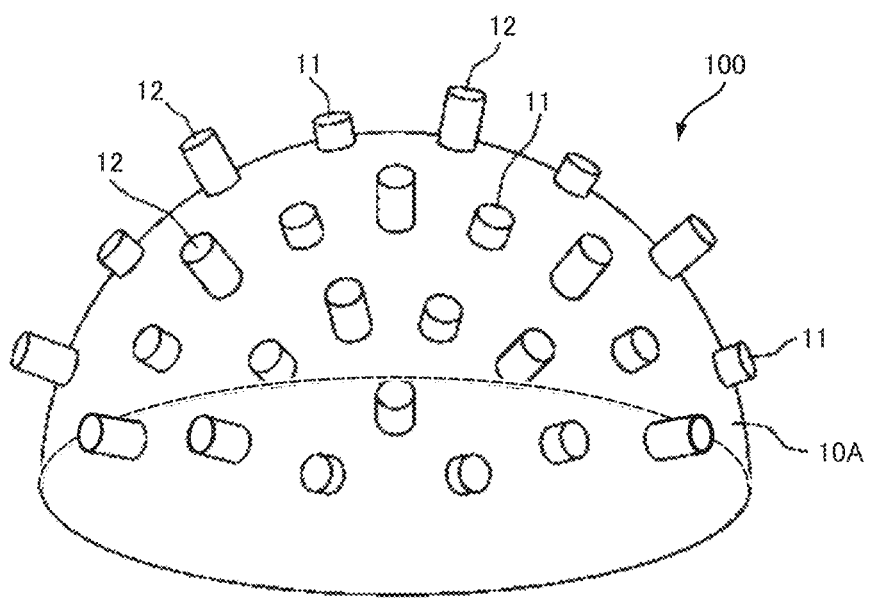
FIG. 21 is a schematic illustration showing a brain cap as a brain activity detecting device detecting brain activities.

FIG. 21 is a schematic illustration showing a brain cap detecting signals indicating a brain activity at a prescribed area in the brain of the subject.

Brain cap 10 includes a cap-shaped holder 10A covering one's skull, and a plurality of (for example, several to several hundreds of) first sensors 11 and second sensors 12 provided on an outer circumferential surface of holder 10A. In FIG. 21, for simplicity of description, sensors are schematically shown spaced by an individual space from each other. Actually, the first and second sensors 11 and 12 are arranged relatively dense at an equal pitch (for example, at an interval of about few millimeters).

If the signals representing brain activity of the subject are to be detected from a limited area, the first and second sensors may be provided only on a specific area of holder 10A of brain cap 10.

First sensor 11 is, for example, an electroencephalogram (EEG) sensor for measuring electric activity generated by brain activity in a non-invasive manner. Each first sensor 11 serves as an electroencephalogram (EEG) and each sensor 11 measures and outputs as an electric signal time-change in brain magnetic field accompanying brain activity at the arranged position. The first sensor 11 has high temporal resolution and capable of measurement in millisecond order.

The second sensor 12 is, for example, a near-infrared sensor NIRS. Each second sensor has a light emitting element emitting near infrared light of relatively short wavelength, and a light receiving element receiving the reflected infrared light. Each second sensor 12 detects amount of absorption of the light emitted from the light emitting element in accordance with the intensity of light received by the light receiving element, and from the output signal of the light receiving element, measures the state of brain blood flow in a non-invasive manner. Unlike electric field or magnetic field, the second sensor 12 is free from the influence of other areas and, therefore, it has superior spatial resolution and it is capable of measurement in the order of a few millimeters or tens of millimeters.

The first and second sensors 11 and 12 as such enable monitoring of the brain activity with small size. Therefore, these sensors can be mounted easily on brain cap 10 such as described above. Measurement of in-brain activity patterns of a subject does not require any large apparatus.

In the present embodiment, utilizing the brain cap 10 shown in FIG. 21, brain activities of a subject are time-sequentially observed, and based on the observational data, brain activities of the subject are predicted.

FIG. 22 is a functional block diagram of a training apparatus 2000 in accordance with the second embodiment.

Training apparatus 2000 in accordance with the second embodiment differs from training apparatus 1000 in accordance with the first embodiment in the following points.

First difference is that brain cap 100 such as described above is used as the detector for detecting brain activities.

The second difference is that in place of processing device 102 shown in FIG. 1, the apparatus includes a training terminal 106 connected to brain cap 100, and a processing device 302 capable of wireless communication with training terminal 106, for performing a prescribed processing on measurement signals received from the training terminal and thereby calculating presentation information and transmitting it in wireless manner to training terminal 106.

Training terminal 106 includes: a display device 130 similar to the one used in the first embodiment; a computing unit 128 converting the measurement signals from brain cap 100 to a prescribed transmission format; and a communication unit 126 transmitting the signals converted to the transmission format to processing device 302 and receiving the presentation information as the feedback information from processing device 302. Computing unit 128 further generates visual information based on the presentation information received by communication unit 126 and presents it to the subject through display device 130.

Processing device 302 includes, in place of input I/F 110 and output I/F 124 shown in FIG. 1, an input/output I/F 111 for wireless communication to and from training terminal 106, a computing device 312 having a similar configuration as computing device 112 of FIG. 1, and a storage device 114 storing a program executed by computing device 312.

The present embodiment is characterized in that training terminal 106 and processing device 302 are separate bodies, and hence, brain cap 100 can be used at a location far from the processing device 302. Therefore, the communication method between training terminal 106 and processing device 302 is not limited to wireless communication simply connecting the two devices directly. By way of example, communication through a network may be available. Direct cable connection between the two is also possible.

In the present embodiment, the presentation information corresponding to the reward value is generated by the side of processing device 302. The present invention, however, is not limited to such an embodiment. Processing device 302 may calculate the reward value, and on the side of training terminal 106, computing unit 128 may receive the reward value and generate the presentation information by a prescribed computation.

Similar to computing device 112 of FIG. 1, computing device 312 includes decoding unit 116, determining unit 118, reward calculating unit 120 and presentation information generating unit 122. Different from computing device 112 of FIG. 1, however, it further includes a pre-processing unit 113 receiving and processing the measurement signals transmitted from training terminal 106 through input/output I/F 111 and generating signals of a format decodable by decoding unit 116.

Specifically, in training apparatus 2000 in accordance with the second embodiment, the functions attained by brain activity detecting device 108 for detecting brain activities at a prescribed area within the brain in the first embodiment are realized by brain cap 100, training terminal 106 and pre-processing unit 113.

Except for these points, the configuration is the same as that of training apparatus 1000 in accordance with the first embodiment and, therefore, description thereof will not be repeated.

By the configuration as described above, training apparatus 2000 in accordance with the second embodiment attains, in addition to the effects attained by training apparatus 1000 in accordance with the first embodiment, the effect that the activities of the subject are not limited by the location of training apparatus 2000, since the subject can be trained wearing brain cap 100 and holding training terminal 106 smaller than processing device 102. Further, display device 130 can be reduced in size, since it has only to display the feedback information. It is noted that training apparatus 2000 in accordance with the second embodiment can also be used as the apparatus for supporting brain function enhancement, as does the training apparatus 1000 in accordance with the first embodiment.

The embodiments as have been described here are mere examples and should not be interpreted as restrictive. The scope of the present invention is determined by each of the claims with appropriate consideration of the written description of the embodiments and embraces modifications within the meaning of, and equivalent to, the languages in the claims.

INDUSTRIAL APPLICABILITY

The apparatus for supporting brain function enhancement in accordance with the present invention can be applied to perceptual learning, rehabilitation, sports relaxation, and adaptive learning with respect to environment.

REFERENCE SIGNS LIST 102, 302 processing device; 106 training terminal; 108 brain activity 2 detecting device; 110 input I/F; 111 input/output I/F; 112, 312 computing device; 113 pre-processing unit; 114 storage device; 116 decoding unit; 118 determining unit; 120 reward calculating unit; 122 presentation information generating unit; 124 output I/F; 128 computing unit; 130 display device; 1000, 2000 training apparatus.

The invention claimed is:

1. An apparatus for supporting brain function enhancement of a prescribed brain function by enabling effective learning, comprising:
 a brain activity detecting device for detecting a signal indicating brain activity at a prescribed area within a brain of a subject;
 a storage device storing information of a target class corresponding to a target activity pattern obtained beforehand with respect to brain function enhancement; and
 processing circuitry configured to, during a brain activity decoder configuration stage, perform the following steps
  present, for a predefined time period, the subject with a plurality of stimulus events, where a stimulus event is a perceptual stimulus which activates portions of the subject's brain;
  receive brain activity signals from the brain activity detecting device while the subject is exposed to the plurality of stimulus events, each of the plurality of stimulus events corresponding to one of a plurality of classes including the target class; and
  train, using a machine learning algorithm, the processing circuitry to decode cranial nerve activity patterns from brain activity signals and classify the cranial nerve activity patterns to one of the plurality of classes of activity patterns classified in advance;
 the processing circuitry further configured to, during a neurofeedback stage for training the subject, repeatedly perform the following steps until a predetermined condition is satisfied,
  exposing the subject to a reward stimulus so that the subject tries to increase the reward while maintaining the subject in the absence of the awareness of the relation between the reward stimulus and the target class;
  receiving a brain activity signal inducted by the subject from the brain activity detecting device while the subject is exposed to the reward stimulus;
  deriving, from the received brain activity signal, a current cranial nerve activity pattern;
  calculating a value representing a degree of possibility of said current cranial nerve activity pattern belonging to the target class,
  computing, based on said calculated value, in accordance with degree of similarity of said current cranial nerve activity pattern to said target class, a reward value corresponding to said degree of similarity; and
  altering the reward stimulus to represent a magnitude of said reward value without revealing to the subject the stimulus event corresponding to the target class; and
  outputting said altered reward stimulus to said subject, wherein
 said stimulus event corresponding to the target class is an object of perception leading to an identification problem of which class it is classified to in the brain; and
 said processing circuitry is further configured to calculate likelihood of which class said activation pattern of cranial nerve activity corresponds to.

2. The apparatus for supporting brain function enhancement according to claim 1, wherein the prescribed area within the brain of the subject corresponds to specific portions of the brain.

3. The apparatus for supporting brain function enhancement according to claim 1, wherein said brain activity detecting device includes a functional Magnetic Resonance Imaging device.

4. The apparatus for supporting brain function enhancement according to claim 1, wherein said brain activity detecting device includes a device for measuring electroencephalogram and near infrared light from outside of a skull.

5. A neurofeedback method of supporting brain function enhancement, using a brain activity detecting device for detecting a signal indicating a brain activity at a specific area within the brain of a subject and processing circuitry trained to decode cranial nerve activity patterns from brain activity signals and classify the cranial nerve activity pattern to one of a plurality of classes of activity patterns classified in advance respectively corresponding to stimulus events in association with a possibility, said method comprising the steps of:
 training, during a brain activity decoder configuration stage, said processing circuitry through machine learning such that said plurality of classes includes a target class corresponding to a target activity pattern obtained with respect to brain function enhancement;
 exposing, during a neurofeedback stage for training the subject, the subject to a reward stimulus and asking the subject to increase the reward without the subject having any knowledge of how to alter it;

receiving, during the neurofeedback stage, a brain activity signal induced by the subject from the brain activity detecting device while the subject is exposed to the reward stimulus;

deriving, from the received brain activity signal, a current cranial nerve activity pattern;

classifying, using the trained processing circuitry, said current cranial nerve activity pattern to one of the plurality of classes respectively corresponding to stimulus events presented to the subject prior to said neurofeedback stage;

calculating, based on the current cranial nerve activity pattern, a value representing a degree of possibility of said current cranial nerve activity pattern belonging to said target class;

calculating, in accordance with a degree of similarity of said current cranial nerves activity pattern to said target class, a reward value corresponding to said degree of similarity based on said calculated value;

altering the reward stimulus the subject is exposed to during said neurofeedback stage to represent a magnitude of said reward value, without revealing to the subject the stimulus event corresponding to the target class; and during said neurofeedback stage, presenting the altered reward stimulus to the subject without revealing to the subject the stimulus event corresponding to the target class, wherein said stimulus event corresponding to the target class is an object of perception leading to an identification problem of which class it is classified to in the brain; and said processing circuitry is further configured to calculate likelihood of which class said activation pattern of cranial nerve activity corresponds to.

6. The apparatus for supporting brain function enhancement according to claim 1, wherein said processing circuitry is trained based on a sparse logistic regression; and said degree of possibility is calculated using the sparse logistic regression, said degree of possibility being the likelihood of said current cranial nerve activity pattern belonging to the target class.

7. The neurofeedback method for supporting brain function enhancement according to claim 5, wherein said processing circuitry is trained based on a sparse logistic regression; and said degree of possibility is calculated using the sparse logistic regression, said degree of possibility being the likelihood of said current cranial nerve activity pattern belonging to the target class.

* * * * *